US 7,012,077 B2

(12) United States Patent
Ackermann et al.

(10) Patent No.: US 7,012,077 B2
(45) Date of Patent: Mar. 14, 2006

(54) SUBSTITUTED CYCLOHEXANE DERIVATIVES

(75) Inventors: Jean Ackermann, Riehen (CH); Johannes Aebi, Basel (CH); Henrietta Dehmlow, Grenzach-Wyhlen (DE); Hans-Peter Maerki, Basel (CH); Olivier Morand, Hegenheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 70 days.

(21) Appl. No.: 10/310,559

(22) Filed: Dec. 5, 2002

(65) Prior Publication Data

US 2003/0186984 A1 Oct. 2, 2003

(30) Foreign Application Priority Data

Dec. 20, 2001 (EP) .................. 01130284

(51) Int. Cl.
 *C07D 239/42* (2006.01)
 *A61K 31/505* (2006.01)
 *A61K 31/506* (2006.01)
 *A61P 3/00* (2006.01)
 *A61P 3/06* (2006.01)

(52) U.S. Cl. .............. 514/275; 544/330; 544/331; 544/332; 544/224; 544/238; 544/336; 544/405; 514/252.01; 514/252.1; 514/336; 546/304

(58) Field of Classification Search ........... 544/330, 544/331, 332; 514/275
See application file for complete search history.

(56) References Cited

U.S. PATENT DOCUMENTS

| 3,592,824 A | 7/1971 | Schut |
| 5,455,273 A | 10/1995 | Maier et al. |
| 6,034,275 A | 3/2000 | Aebi et al. |

FOREIGN PATENT DOCUMENTS

| EP | 636367 | 2/1995 |
| EP | 0 778 264 | 6/1997 |
| FR | 1515629 | 1/1968 |
| WO | WO 02 20483 | 3/2002 |
| WO | WO 02 36584 | 5/2002 |

OTHER PUBLICATIONS

Cecil Textbook of Medicine, edited by Bennet, J.C., and Plum F., 20th edition, vol. 1, 1004-1010, 1996.*
Gotto et al., *Circulatio*, vol. 8(5)1, pp. 1721-1733 (1990).
Stein et al., *Nutr. Metab. Cardiovasc. Dis.*, vol. 2, pp. 113-156 (1992).
Illingworth, *Med. Clin. North Am.*, vol. (1), pp. 23-42 (2000).
Ross etal., *Arch. Intern. Med.*, vol. 159, pp. 1793-1802 (1999).
Ellen & McPherson, *J. Cardiol.*, vol. 81, pp. 60B-65B (1998).
Shepherd, *Eur. Heart J.*, vol. 16, pp. 5-13 (1995).
Davignon et al., *Can.J. Cardiol.* vol. 8, pp. 843-864 (1992).
Pedersen and Tobert, *Drug Safety.*, vol. 14, pp. 11-24 (1996).
Morand etal., *J. Lipid Res.*, vol. 38, pp. 373-390 (1997).
Mark et al., *J. Lipid Res.*, vol. 37, pp148-158 (1996).
Peffley et al., *Biochem. Pharmaco.*, vol. 56, pp. 439-449 (1998).
Nelson et al.,*J. Biol. Chem.*, vol. 256, pp. 1067-1068 (198)1.
Spencer et al., *J. Biol. Chem.*, vol. 260, pp. 13391-13394 (1985).
Panini etal., *J. Lipid Res.* vol. 27, pp. 1190-1204 (1986).
Ness et al., *Arch. Biochem. Biophys.* vol. 308, pp. 420-425 (1994).
Janowski etal., *Proc. Natl. Acad. Sci. USA*, vol. 96, pp. 266-271 (1999).
Venkateswaran et al., *J. Biol. Chem.*, vol. 275, pp. 14700-147078 (2000).
Schmidt and Kaminsky, *Front Biosci.* vol. 62, pp. D505-D514 (20012).
Ordovas, *Nutr. Rev.*, vol. 58, pp. 76-79 (2000).
Tobin et al., *Mol. Endocrinol.* vol. 14, pp. 741-751 (2000).
Auwerx et al., Atherosclerosis XII, pp. 21-39 (2000).
Wermuth, et al., Practise of Medicinal Chemistry, XP002190259, Table 13.1, pp. 203-237 (1996).

(Continued)

*Primary Examiner*—Venkataraman Balasubramanian
(74) *Attorney, Agent, or Firm*—George W. Johnston; Patricia S. Rocha-Tramaloni

(57) ABSTRACT

The present invention relates to compounds of formula (I)

wherein $A^1$, $A^2$, $A^3$, $A^4$, $A^5$, $A^6$, U, V, m, n and o are as defined in the specification, and pharmaceutically acceptable salts thereof. The compounds are useful for the treatment and/or prophylaxis of diseases which are associated with the 2,3-oxidosqualene-lanosterol cyclase biosynthetic pathway such as hypercholesterolemia and hyperlipemia.

36 Claims, No Drawings

OTHER PUBLICATIONS

Avenell et al., Bioorg. Med. Chem. Lett. 9, pp. 2715-2720 (1999).
Baker et al., J. Chem. Soc. Perkin Trans. 1, pp. 1415-1421 (1990).
Bartlett et al., J. Am. Chem. Soc. 106, pp. 7854-7860 (1984).
Belostotskii et al., Tetrahedron Letters 35(28), pp. 5075-5076 (1994).
Brown et al., Pyrimidine reactions. XXII. Relative reactivities of corresponding chloro-, bromo-, and iodopyrimidines in aminolysis., J. Chem. Soc. C (1971), 10, 1889-1891.
Chaplinski et al., Angew. Chem. Int. Ed. Engl. 35(4), pp. 413-414 (1996).
Cooper et al., Synthesis 4, pp. 621-625 (2001).
Costet et al., J. Biol Chem. 275, pp. 28240-28245 (2000).
Denton et al., Synlett 1, pp. 55-56 (1999).
Johnston et al., J. of Medicinal Chemistry 20, pp. 279-290 (1977).
Karpavichyus et al., BACCAT; Bull. Acad.Sci. USSR Div. Chem.Sci (Engl. Transl.);EN;29;1980;1689-1694.
Marshall et al., J. Org. Chem. 61(17), pp. 5729-5735 (1996).
Mattson et al., J. Org. Chem. 55, pp. 2552-2554 (1990).
Venuti et al., J. Med. Chem. 30, pp. 303-318 (1987).
Wustrow, D., et al, J. Med. Chem., 41, pp. 760-771 (1998).

* cited by examiner

SUBSTITUTED CYCLOHEXANE DERIVATIVES

BACKGROUND OF THE INVENTION 2,3-oxidosqualene-lanosterol cyclase (EC 5.4.99.) is required for the biosynthesis of cholesterol, ergosterol and other sterols. Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

SUMMARY OF THE INVENTION

The present invention is concerned with novel cyclohexane derivatives, their manufacture and their use as medicaments. In particular, the invention relates to compounds of the formula (I)

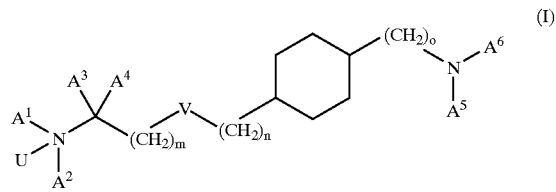

wherein

U is O or a lone pair,

V is a single bond, O, S, —CH=CH—CH$_2$—O—, —CH=CH—, or —C≡C—, m and n independently from each other are 0 to 7 and m+n is 0 to 7, with the proviso that m is not 0 if V is O or S, is 0 to 2

A$^1$ is hydrogen, lower-alkyl, hydroxy-lower-alkyl, or lower-alkenyl,

A$^2$ is lower-alkyl, cycloalkyl, cycloalkyl-lower-alkyl, or lower-alkenyl, optionally substituted by R$^1$, or A$^1$ and A$^2$ are bonded to each other to form a ring and -A$^1$-A$^2$- is lower-alkylene or lower-alkenylene, optionally substituted by R$^1$, in which one —CH$_2$— group of -A$^1$-A$^2$- can optionally be replaced by NR$^2$, S, or O, A$^3$ and A$^4$ independently from each other are hydrogen or lower-alkyl, or A$^3$ and A$^4$ are bonded to each other to form a ring together with the carbon atom to which they are attached and -A$^3$-A$^4$- is —(CH$_2$)$_{2-5}$—, A$^5$ is hydrogen, lower-alkyl, or lower-alkenyl, A$^6$ is pyridinyl, pyridazinyl, pyrimidinyl or pyrazinyl, optionally substituted with 1 or 2 substituents independently selected from the group consisting of lower-alkyl, lower-alkyl-cycloalkyl, thio-lower-alkoxy, cycloalkyl, carbamoyl, carboxy, carboxy-lower-alkyl, cyano, amino, mono- and dialkylamino, lower-alkoxy, lower-alkoxy-lower-alkyl, lower-alkoxy-carbonyl, lower-alkoxy-carbonyl-lower-alkyl, lower-alkenyl, lower-alkynyl, aryl, aryl-lower-alkyl, aryloxy, halogen, heteroaryl, heterocyclyl, heterocyclyl-lower-alkyl and trifluoromethyl, R$^1$ is hydroxy, hydroxy-lower-alkyl, lower-alkoxy, lower-alkoxycarbonyl, halogen, CN, N(R$^3$,R$^4$), or thio-lower-alkoxy, R$^2$, R$^3$, and R$^4$ independently from each other are hydrogen or lower-alkyl, and pharmaceutically acceptable salts thereof, with the proviso, that the compound of formula (I) is not trans-[4-(2-Dipropylamino-ethyl)-cyclohexyl]-pyrimidin-2-yl-amine.

The compounds of the present invention are useful for the treatment and/or prophylaxis of diseases associated with 2,3-oxidosqualine-lanosterol cyclase such as hypercholesterolemia and hyperlipemia.

DETAILED DESCRIPTION OF THE INVENTION

In detail, the present invention relates to compounds of formula (I)

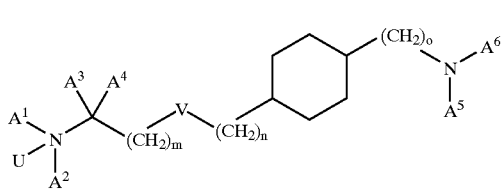

wherein

U is O or a lone pair,

V is a single bond, O, S, —CH=CH—CH$_2$—O—, —CH=CH—, or —C≡C—, m and n independently from each other are 0 to 7 and m+n is 0 to 7, with the proviso that m is not 0 if V is O or S, is 0 to 2

A$^1$ is hydrogen, lower-alkyl, hydroxy-lower-alkyl, or lower-alkenyl,

A$^2$ is lower-alkyl, cycloalkyl, cycloalkyl-lower-alkyl, or lower-alkenyl, optionally substituted by R$^1$, or A$^1$ and A$^2$ are bonded to each other to form a ring and -A$^1$-A$^2$- is lower-alkylene or lower-alkenylene, optionally substituted by R$^1$, in which one —CH$_2$— group of -A$^1$-A$^2$- can optionally be replaced by NR$^2$, S, or O, A$^3$ and A$^4$ independently from each other are hydrogen or lower-alkyl, or A$^3$ and A$^4$ are bonded to each other to form a ring together with the carbon atom to which they are attached and -A$^3$-A$^4$- is —(CH$_2$)$_{2-5}$—, A$^5$ is hydrogen, lower-alkyl, or lower-alkenyl, A$^6$ is pyridinyl, pyridazinyl, pyrimidinyl or pyrazinyl, optionally substituted with 1 or 2 substituents independently selected from the group consisting of lower-alkyl, lower-alkyl-cycloalkyl, thio-lower-alkoxy, cycloalkyl, carbamoyl, carboxy, carboxy-lower-alkyl, cyano, amino, mono- and dialkylamino, lower-alkoxy, lower-alkoxy-lower-alkyl, lower-alkoxy-carbonyl, lower-alkoxy-carbonyl-lower-alkyl, lower-alkenyl, lower-alkynyl, aryl, aryl-lower-alkyl, aryloxy, halogen, heteroaryl, heterocyclyl, heterocyclyl-lower-alkyl and trifluoromethyl, R$^1$ is hydroxy, hydroxy-lower-alkyl, lower-alkoxy, lower-alkoxycarbonyl, halogen, CN, N(R$^3$,R$^4$), or thio-lower-alkoxy, R$^2$, R$^3$, and R$^4$ independently from each other are hydrogen or lower-alkyl, and pharmaceutically acceptable salts thereof, with the proviso, that the compound of formula (I) is not trans-[4-(2-Dipropylamino-ethyl)-cyclohexyl]-pyrimidin-2-yl-amine.

The present compounds of formula I inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl. The term "thioalkoxy" refers to the group R'—S—, wherein R' is an alkyl. The term "thio-lower-alkoxy" refers to the group R'—S—, wherein R' is a lower-alkyl.

The term "alkenyl", alone or in combination with other groups, stands for a straight-chain or branched hydrocarbon residue comprising an olefinic bond and up to 20, preferably up to 16 carbon atoms, more preferrably up to 10 carbon atoms. Lower-alkenyl groups as described below also are preferred alkenyl groups. The term "lower-alkenyl" refers to a straight-chain or branched hydrocarbon residue comprising an olefinic bond and up to 7, preferably up to 4 carbon atoms, such as e.g. 2-propenyl.

The term "alkynyl", alone or in combination with other groups, stands for a straight-chain or branched hydrocarbon residue comprising a triple bond and up to 20, preferably up to 16 carbon atoms, more preferably up to 10 carbon atoms. Lower-alkynyl groups as described below also are preferred alkynyl groups. The term "lower-alkynyl" refers to a straight-chain or branched hydrocarbon residue comprising a triple bond and up to 7, preferably up to 4 carbon atoms, such as e.g. 2-propinyl.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "alkenylene" refers to a straight chain or branched divalent hydrocarbon group comprising an olefinic bond and up to 20 carbon atoms, preferably up to 16 carbon atoms, more preferably up to 10 carbon atoms. Lower-alkenylene groups as described below also are preferred alkenylene groups. The term "lower-alkenylene" refers to a straight chain or branched divalent hydrocarbon group comprising an olefinic bond and up to 7, preferably up to 5, C-atoms. Straight chain alkenylene or lower-alkenylene groups are preferred.

The term "aryl" relates to the phenyl or naphthyl group, preferably the phenyl group, which can optionally be substituted by 1 to 3 substituents independently selected from the group consisting of lower-alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl. Preferred substituents are halogen, $CF_3$, CN, lower-alkyl and/or lower-alkoxy.

The term "heteroaryl" refers to an aromatic 5- or 6-membered ring which can comprise 1, 2 or 3 atoms selected from nitrogen, oxygen and/or sulphur, such as furyl, pyridyl, pyridazinyl, pyrimidinyl, pyrazinyl, thienyl, isoxazolyl, oxazolyl, imidazolyl, or pyrrolyl. A heteroaryl group may have a substitution pattern as described earlier in connection with the term "aryl".

The term "heterocyclyl" as used herein denotes non-aromatic monocyclic heterocycles with 5 or 6 ring members, which comprise 1, 2 or 3 hetero atoms selected from nitrogen, oxygen and sulfur. Examples of suitable heterocycles are pyrrolidinyl, pyrrolinyl, imidazolidinyl, imidazolinyl, pyrazolidinyl, pyrazolinyl, piperidyl, piperazinyl, morpholinyl, pyranyl, 4,5-dihydro-oxazolyl, 4,5-dihydro-thiazolyl. A heterocyclyl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms. Preferred salts are phosphates, citrates, fumarates, formates, hydrochlorides, hydrobromides and methanesulfonic acid salts.

Preferred are compounds of formula (I) and/or pharmaceutically acceptable salts thereof. Other preferred embodiments relate to compounds of formula (I) wherein U is a lone pair or to compounds of formula (I) wherein U is O.

Compounds of formula (I) as described above, in which V is a single bond, O, —CH=CH—CH$_2$—O—, or —C≡C— relate to a preferred embodiment of the present invention. More preferred compounds as defined above are those, wherein V is —C≡C—.

In a further preferred embodiment of the present invention, m is 0 to 3, more preferably m is 0. Compounds of formula (I), in which n is 0 or 1 are also preferred, with those compounds wherein n is 0 being more preferred. Compounds as decsribed above, in which the number of carbon atoms of $(CH_2)_m$, V and $(CH_2)_n$ together is 7 or less, are also preferred. Other preferred compounds of formula (I) as described above are those, wherein o is 0 or 1.

Other preferred compounds of the present invention are those in which $A^1$ represents lower-alkyl, preferrably those in which $A^1$ is methyl or ethyl. Another group of preferred compounds of the present invention are those in which $A^2$ represents lower-alkenyl, or lower-alkyl optionally substituted by $R^2$, wherein $R^2$ is hydroxy or lower-alkoxy, with those compounds wherein $A^2$ represents methyl, propyl or 2-hydroxy-ethyl being especially preferred.

Compounds of formula (I), wherein $A^1$ and $A^2$ are bonded to each other to form a ring and -$A^1$-$A^2$- is lower-alkylene are also preferred, with those compounds, wherein -$A^1$-$A^2$- is —(CH$_2$)$_5$— being especially preferred.

In compounds wherein $A^1$ and $A^2$ are bonded to each other to form a ring, said ring is preferably a 4-, 5-, or 6-membered ring such as e.g. piperidinyl or pyrrolidinyl.

A further preferred embodiment of the present invention relates to compounds of formula (I), wherein $A^3$ and $A^4$ represent hydrogen.

Compounds of formula (I), wherein $A^5$ is hydrogen or lower-alkyl also relate to a preferred embodiment of the present invention, with those compounds, wherein $A^5$ is methyl relating to a particularly preferred embodiment. Other preferred compounds are those in which $A^6$ is pyridinyl, pyridazinyl, pyrimidinyl or pyrazinyl, optionally substituted with 1 or 2 substituents independently selected from the group consisting of lower-alkyl, lower-alkoxy, halogen, pyridyl and thienyl. More preferred compounds of formula (I) are those wherein $A^6$ is pyridazinyl or pyrimidinyl, optionally substituted with 1 or 2 substituents independently selected from the group consisting of bromo, chloro, ethyl and pyridyl, with those compounds wherein $A^6$ is 5-bromo-pyrimidin- 2-yl, 6-chloro-pyridazin-3-yl, 5-chloro-pyrimidin-2-yl, 5-pyridin-4-yl-pyrimidin-2-yl, 5-ethyl-pyrimidin-2-yl being particularly preferred.

Preferred compounds of general formula (I) are those selected from the group consisting of Trans-{4-[3-(Allyl-methyl-amino)-prop-1-ynyl]-cyclohexyl}-(5-bromo-pyrimidin-2-yl)-methyl-amine,
Trans-(5-Bromo-pyrimidin-2-yl)-methyl-{4-[3-(methyl-propyl-amino)-prop-1-ynyl]-cyclohexyl}-amine,
Trans-(5-Bromo-pyrimidin-2-yl)-[4-(3-dimethylamino-prop-1-ynyl)-cyclohexyl]-methyl-amine,
Trans-(5-Bromo-pyrimidin-2-yl)-(4-{3-[ethyl-(2-methoxy-ethyl)-amino]-prop-1-ynyl}-cyclohexyl)-methyl-amine,
Trans-{4-[3-(Allyl-methyl-amino)-propyl]-cyclohexyl}-(5-bromo-pyrimidin-2-yl)-methyl-amine,
Trans-(5-Bromo-pyrimidin-2-yl)-methyl-{4-[3-(methyl-propyl-amino)-propyl]-cyclohexyl}-amine,
Trans-(5-Bromo-pyrimidin-2-yl)-[4-(3-dimethylamino-propyl)-cyclohexyl]-methyl-amine,
Trans-(5-Bromo-pyrimidin-2-yl)-(4-{3-[ethyl-(2-methoxy-ethyl)-amino]-propyl}-cyclohexyl)-methyl-amine,
Trans-[4-(3-Dimethylamino-prop-1-ynyl)-cyclohexyl]-methyl-pyrimidin-2-yl-amine,
Trans-(6-Chloro-pyridazin-3-yl)-[4-(3-dimethylamino-prop-1-ynyl)-cyclohexyl]-methyl-amine,
Trans-(5-Chloro-pyrimidin-2-yl)-[4-(3-dimethylamino-prop-1-ynyl)-cyclohexyl]-methyl-amine,
Trans-(5-Bromo-pyridin-2-yl)-[4-(3-dimethylamino-prop-1-ynyl)-cyclohexyl]-methyl-amine,
Trans-[4-(3-Dimethylamino-prop-1-ynyl)-cyclohexyl]-methyl-pyridin-2-yl-amine,
Trans-[4-(3-Dimethylamino-prop-1-ynyl)-cyclohexyl]-methyl-pyrazin-2-yl-amine,
trans-[2-[(3-{4-[(5-Bromo-pyrimidin-2-yl)-methyl-amino]-cyclohexyl}-prop-2-ynyl)-ethyl-amino]-ethanol],
trans-[(5-Bromo-pyrimidin-2-yl)-methyl-[4-(3-piperidin-1-yl-prop-1-ynyl)-cyclohexyl]-amine],
trans-[(5-Bromo-pyrimidin-2-yl)-[4-(3-diethylamino-prop-1-ynyl)-cyclohexyl]-methyl-amine],
Trans-2-[(3-{4-[(6-Chloro-pyridazin-3-yl)-methyl-amino]-cyclohexyl}-prop-2-ynyl)-ethyl-amino]-ethanol,
Trans-2-[(3-{4-[(5-Chloro-pyrimidin-2-yl)-methyl-amino]-cyclohexyl}-prop-2-ynyl)-ethyl-amino]-ethanol,
Trans-2-[(3-{4-[(5-Bromo-pyridin-2-yl)-methyl-amino]-cyclohexyl}-prop-2-ynyl)-ethyl-amino]-ethanol,
trans-[4-(3-Dimethylamino-prop-1-ynyl)-cyclohexyl]-methyl-(5-pyridin-4-yl-pyrimidin-2-yl)-amine,
trans-[4-(3-Dimethylamino-prop-1-ynyl)-cyclohexyl]-methyl-(5-thiophen-3-yl-pyrimidin-2-yl)-amine,
Trans-6-(Methyl-{4-[3-(methyl-propyl-amino)-prop-1-ynyl]-cyclohexyl}-amino)-nicotinonitrile,
Trans-6-{Methyl-[4-(3-piperidin-1-yl-prop-1-ynyl)-cyclohexyl]-amino}-nicotinonitrile,
Trans-6-{[4-(3-Dimethylamino-prop-1-ynyl)-cyclohexyl]-methyl-amino}-nicotinonitrile,
Trans-(5-Ethyl-pyrimidin-2-yl)-methyl-[4-(3-piperidin-1-yl-prop-1-ynyl)-cyclohexyl]-amine,
Trans-[4-(3-Dimethylamino-prop-1-ynyl)-cyclohexyl]-(5-ethyl-pyrimidin-2-yl)-methyl-amine,
Trans-(5-Bromo-pyrimidin-2-yl)-[4-(4-dimethylamino-but-1-ynyl)-cyclohexyl]-methyl-amine,
Trans-(6-Chloro-pyridazin-3-yl)-methyl-[4-(3-piperidin-1-yl-prop-1-ynyl)-cyclohexyl]-amine,
Trans-(5-Chloro-pyrimidin-2-yl)-methyl-[4-(3-piperidin-1-yl-prop-1-ynyl)-cyclohexyl]-amine,
Trans-(5-Bromo-pyrimidin-2-yl)-[4-(4-dimethylamino-butyl)-cyclohexyl]-methyl-amine,
Trans-(5-Bromo-pyrimidin-2-yl)-[2-(4-dimethylaminomethyl-cyclohexyl)-ethyl]-amine,
Trans-(5-Bromo-pyrimidin-2-yl)-methyl-[4-(4-piperidin-1-yl-but-1-ynyl)-cyclohexyl]-amine,
Trans-(2E)-(5-Bromo-pyrimidin-2-yl)-[4-(4-dimethylamino-but-2-enyloxy)-cyclohexyl]-methyl-amine,
Trans-(2E)-(5-Bromo-pyrimidin-2-yl)-methyl-[4-(4-piperidin-1-yl-but-2-enyloxy)-cyclohexyl]-amine,
Trans-(6-Chloro-pyridazin-3-yl)-methyl-[4-(3-pyrrolidin-1-yl-prop-1-ynyl)-cyclohexyl]-amine,
Trans-(5-Bromo-pyrimidin-2-yl)-methyl-[4-(4-piperidin-1-yl-butyl)-cyclohexyl]-amine,
Trans-(5-Bromo-pyrimidin-2-yl)-[2-(4-piperidin-1-ylmethyl-cyclohexyl)-ethyl]-amine,
Trans-(6-Chloro-pyridazin-3-yl)-methyl-{4-[3-(methyl-propyl-amino)-prop-1-ynyl]-cyclohexyl}-amine,
Trans-(6-Chloro-pyridazin-3-yl)-[4-(3-diethylamino-prop-1-ynyl)-cyclohexyl]-methyl-amine,
Trans-(6-Chloro-pyridazin-3-yl)-[4-(4-dimethylamino-but-2-ynyl)-cyclohexyl]-methyl-amine,
Trans-(6-Chloro-pyridazin-3-yl)-methyl-[4-(4-piperidin-1-yl-but-2-ynyl)-cyclohexyl]-amine,
Trans-(5-Bromo-pyrimidin-2-yl)-[4-(4-dimethylamino-but-2-ynyl)-cyclohexyl]-methyl-amine,
Trans-(5-Bromo-pyrimidin-2-yl)-methyl-[4-(4-piperidin-1-yl-but-2-ynyl)-cyclohexyl]-amine,
Trans-(5-Bromo-pyrimidin-2-yl)-methyl-[4-(2-pyrrolidin-1-yl-ethoxy)-cyclohexyl]-amine,
Trans-(5-Bromo-pyrimidin-2-yl)-[2-(4-dimethylaminomethyl-cyclohexyl)-ethyl]-methyl-amine,
Trans-(5-Bromo-pyrimidin-2-yl)-methyl-[2-(4-piperidin-1-ylmethyl-cyclohexyl)-ethyl]-amine,
Trans-[4-(3-Dimethylamino-prop-1-ynyl)-cyclohexyl]-methyl-(6-methyl-pyridazin-3-yl)-amine,
Trans-2-[Ethyl-(3-{4-[methyl-(6-methyl-pyridazin-3-yl)-amino]-cyclohexyl}-prop-2-ynyl)-amino]-ethanol,
Trans-[4-(3-Dimethylamino-prop-1-ynyl)-cyclohexyl]-(6-methoxy-pyridazin-3-yl)-methyl-amine,
trans-(5-Bromo-pyrimidin-2-yl)-[4-(3-dimethylamino-prop-1-ynyl)-cyclohexylmethyl]-methyl-amine,
trans-2-{[3-(4-{[(5-Bromo-pyrimidin-2-yl)-methyl-amino]-methyl}-cyclohexyl)-prop-2-ynyl]-ethyl-amino}-ethanol,
trans-(5-Bromo-pyrimidin-2-yl)-methyl-[4-(3-piperidin-1-yl-prop-1-ynyl)-cyclohexylmethyl]-amine,
trans-[4-(3-Dimethylamino-prop-1-ynyl)-cyclohexylmethyl]-(5-ethyl-pyrimidin-2-yl)-methyl-amine,
trans-2-{Ethyl-[3-(4-{[(5-ethyl-pyrimidin-2-yl)-methyl-amino]-methyl}-cyclohexyl)-prop-2-ynyl]-amino}-ethanol,
trans(5-Ethyl-pyrimidin-2-yl)-methyl-[4-(3-piperidin-1-yl-prop-1-ynyl)-cyclohexylmethyl]-amine,
trans-(6-Chloro-pyridazin-3-yl)-[4-(3-dimethylamino-prop-1-ynyl)-cyclohexylmethyl]-methyl-amine,
trans-2-{[3-(4-{[(6-Chloro-pyridazin-3-yl)-methyl-amino]-methyl}-cyclohexyl)-prop-2-ynyl]-ethyl-amino}-ethanol,
trans-(6-Chloro-pyridazin-3-yl)-methyl-[4-(3-piperidin-1-yl-prop-1-ynyl)-cyclohexylmethyl]-amine,
trans-2-[(4-{2-[(5-Bromo-pyrimidin-2-yl)-methyl-amino]-ethyl}-cyclohexylmethyl)-ethyl-amino]-ethanol, trans-[4-(3-Dimethylamino-prop-1-ynyl)-cyclohexylmethyl]-methyl-(5-propyl-pyrimidin-2-yl)-amine,
trans-2-{Ethyl-[3-(4-{[methyl-(5-propyl-pyrimidin-2-yl)-amino]-methyl}-cyclohexyl)-prop-2-ynyl]-amino}-ethanol,
trans-(5-Chloro-pyrimidin-2-yl)-[4-(3-dimethylamino-prop-1-ynyl)-cyclohexylmethyl]-methyl-amine,
trans-2-{[3-(4-{[(5-Chloro-pyrimidin-2-yl)-methyl-amino]-methyl}-cyclohexyl)-prop-2-ynyl]-ethyl-amino }-ethanol,
trans-3-[(4-{2-[(5-Bromo-pyrimidin-2-yl)-methyl-amino]-ethyl}-cyclohexylmethyl)-amino]-propan-1-ol, and
trans-3-[(4-{2-[(5-Bromo-pyrimidin-2-yl)-methyl-amino]-ethyl}-cyclohexylmethyl)-methyl-amino]-propan-1-ol, and pharmaceutically acceptable salts thereof.

Particularly preferred compounds of general formula (I) are those selected from the group consisting of
Trans-(5-Bromo-pyrimidin-2-yl)-methyl-{4-[3-(methyl-propyl-amino)-prop-1-ynyl]-cyclohexyl}-amine,
Trans-(5-Bromo-pyrimidin-2-yl)-[4-(3-dimethylamino-prop-1-ynyl)-cyclohexyl]-methyl-amine,
Trans-(6-Chloro-pyridazin-3-yl)-[4-(3-dimethylamino-prop-1-ynyl)-cyclohexyl]-methyl-amine,
Trans-(5-Chloro-pyrimidin-2-yl)-[4-(3-dimethylamino-prop-1-ynyl)-cyclohexyl]-methyl-amine,
Trans-[(5-Bromo-pyrimidin-2-yl)-methyl-[4-(3-piperidin-1-yl-prop-1-ynyl)-cyclohexyl]-amine],
Trans-[4-(3-Dimethylamino-prop-1-ynyl)-cyclohexyl]-methyl-(5-pyridin-4-yl-pyrimidin-2-yl)-amine,
Trans-[4-(3-Dimethylamino-prop-1-ynyl)-cyclohexyl]-(5-ethyl-pyrimidin-2-yl)-methyl-amine,
Trans-(5-Bromo-pyrimidin-2-yl)-[4-(3-dimethylamino-prop-1-ynyl)-cyclohexylmethyl]-methyl-amine,
Trans-2-{[3-(4-{[(5-Bromo-pyrimidin-2-yl)-methyl-amino]-methyl}-cyclohexyl)-prop-2-ynyl]-ethyl-amino}-ethanol,
Trans-2-{Ethyl-[3-(4-{[(5-ethyl-pyrimidin-2-yl)-methyl-amino]-methyl}-cyclohexyl)-prop-2-ynyl]-amino}-ethanol,
Trans(5-Ethyl-pyrimidin-2-yl)-methyl-[4-(3-piperidin-1-yl-prop-1-ynyl)-cyclohexylmethyl]-amine, and
Trans-2-{[3-(4-{[(6-Chloro-pyridazin-3-yl)-methyl-amino]-methyl}-cyclohexyl)-prop-2-ynyl]-ethyl-amino}-ethanol, and pharmaceutically acceptable salts thereof Compounds of formula (I) can have one or more asymmetric carbon atoms and can exist in the form of optically pure enantiomers or as racemats. They can exist as cis- or trans-isomers. The invention embraces all of these forms. Compounds of formula (I) which are trans-isomers (with reference to the cyclohexyl ring) are preferred.

It will be appreciated, that the compounds of general formula (I) in this invention may be derivatised at functional groups to provide derivatives which are capable of conversion back to the parent compound in vivo.

The present invention also relates to a process for the manufacture of compounds of formula (I) as described above, which process comprises reacting a compound of formula (II)

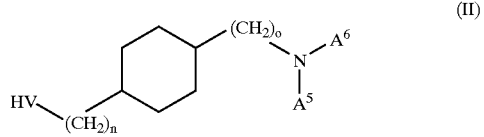

(II)

with a compound $(A^1, A^2, U)N—C(A^3, A^4)-(CH_2)_m-M$, wherein V is O or S, M is mesylate, tosylate, triflate, Cl, Br or I, and U, $A^1$, $A^2$, $A^3$, $A^4$, $A^5$, $A^6$, m, n and o are as defined above, or wherein HV is mesylate, tosylate, triflate, Cl, Br or I, and M is OH, SH, or b) reacting a compound of formula (III)

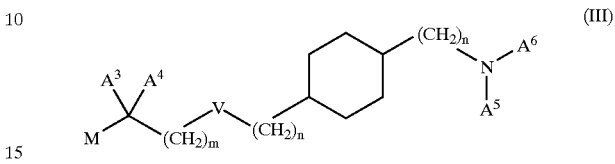

(III)

with a compound $NHA^1A^2$, wherein M is mesylate, tosylate, triflate, Cl, Br or I, and $A^1$, $A^2$, $A^3$, $A^4$, $A^5$, $A^6$, V, m, n and o are as defined above, and optionally converting a compound of formula (I) as defined above to a pharmaceutically acceptable salt, and optionally converting a compound of formula (I) as defined above, wherein U is a lone pair, to a corresponding compound wherein U is O.

Reactions of a compound of formula (II) with a compound $(A^1, A^2, U)N—C(A^3, A^4)-(CH_2)_m-M$ can be carried out by procedures known in the art and described in Scheme 5 in a solvent like N,N-dimethylformamide, N,N-dimethylacetamide or nitromethane in the presence of a base like sodium hydride or 2,6-di-tert-butylpyridine in a temperature range of e.g. 0° C. to 80° C. Reactions of a compound of formula (III) with a compound $NHA^1A^2$ can be carried out by procedures known in the art and described in the examples preferentially in solvents like N,N-dimethylacetamide, N,N-dimethylformamide or methanol, preferentially between room temperature and 80° C. A compound as defined above can be converted to a pharmaceutically acceptable salt by procedures known in the art such as by a treatment with a corresponding acid in a solvent like ethanol, methanol or dichloromethane in a temperature range of e.g. −20° C. and +40° C. A compound as defined above, wherein U is a lone pair can can be converted to a compound wherein U is 0 by procedures known in the art such as by reaction with a mixture of hydrogen peroxide urea adduct and phthalic anhydride in dichloromethane at room temperature.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

Scheme 1

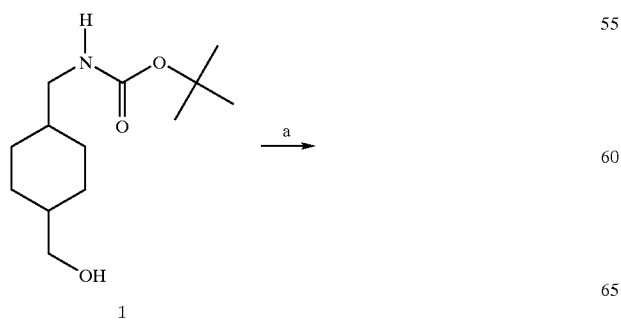

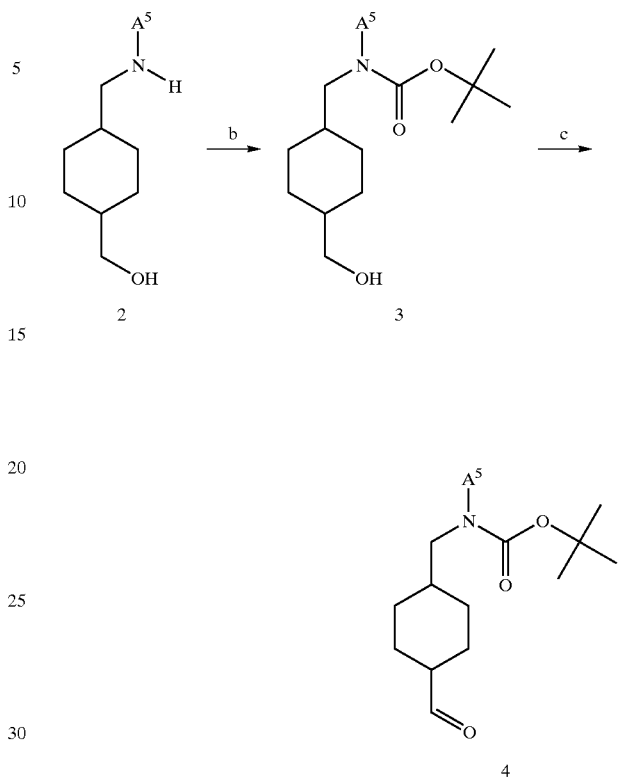

Scheme 2

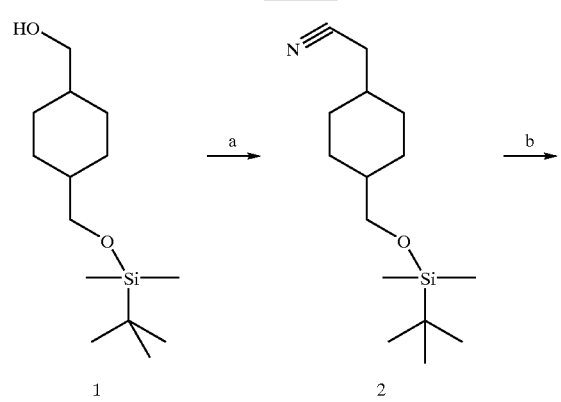

13
-continued
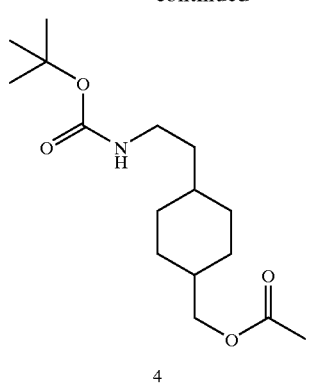
4
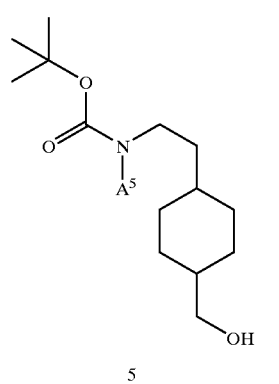
5
Scheme 3
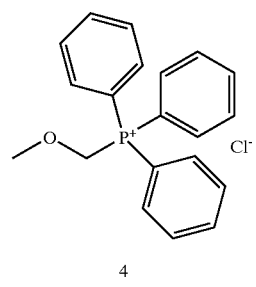
4
14
-continued
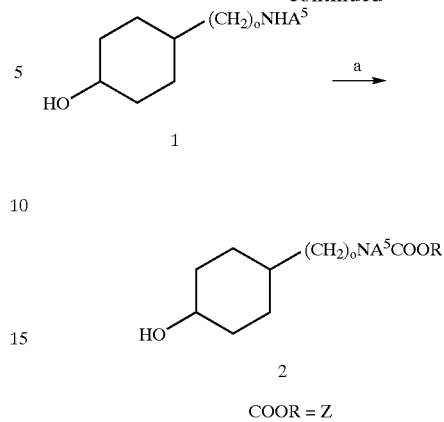
1
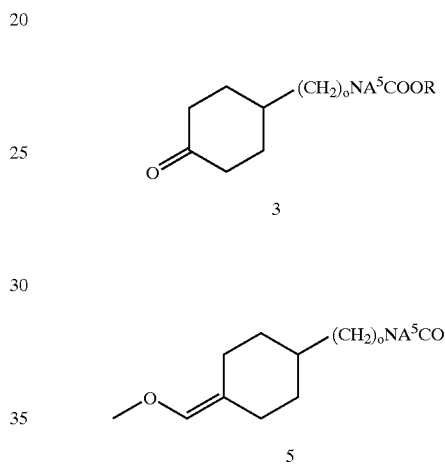
2
COOR = Z
3
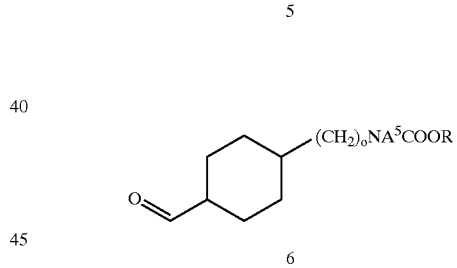
5
6
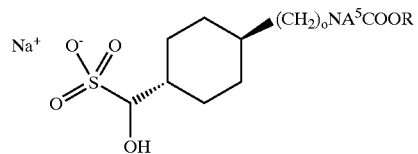
7
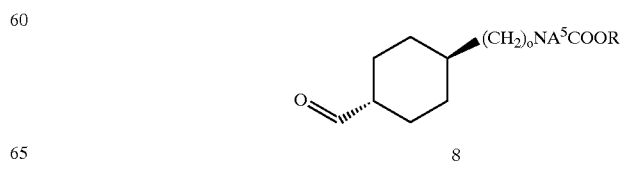
8

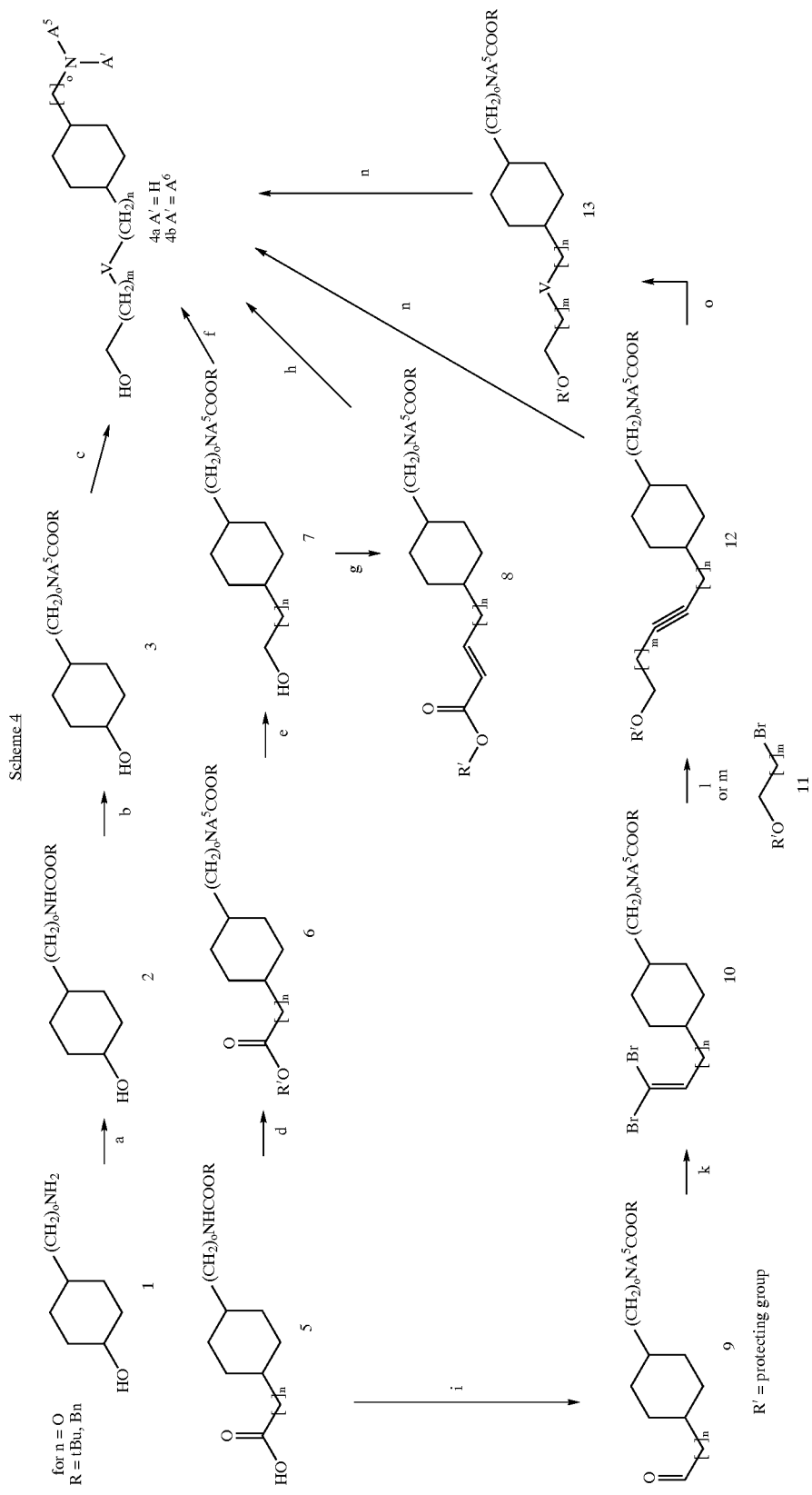

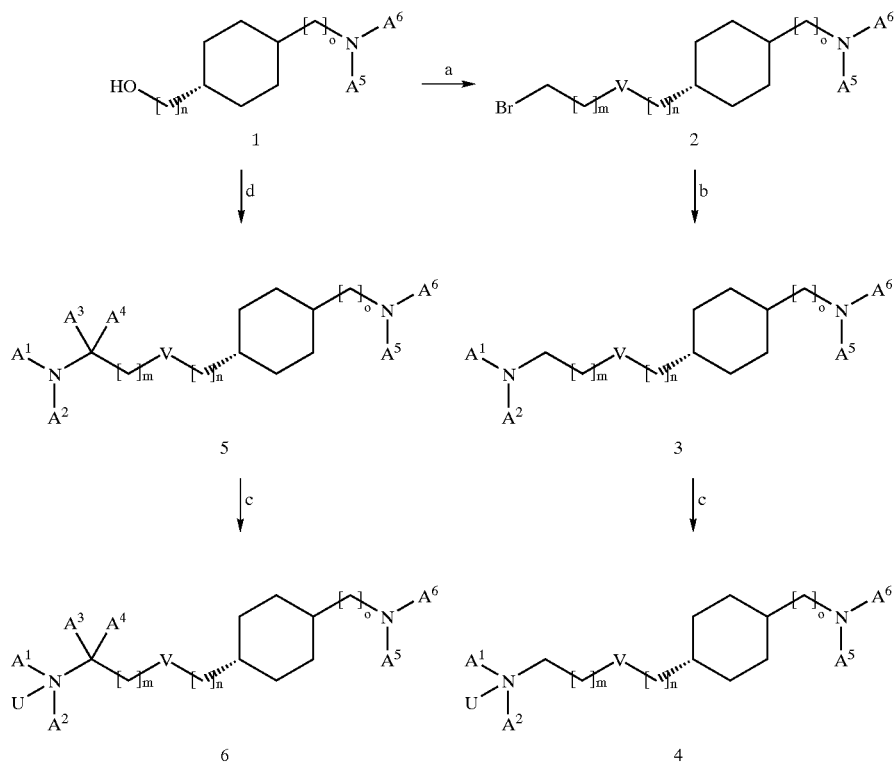
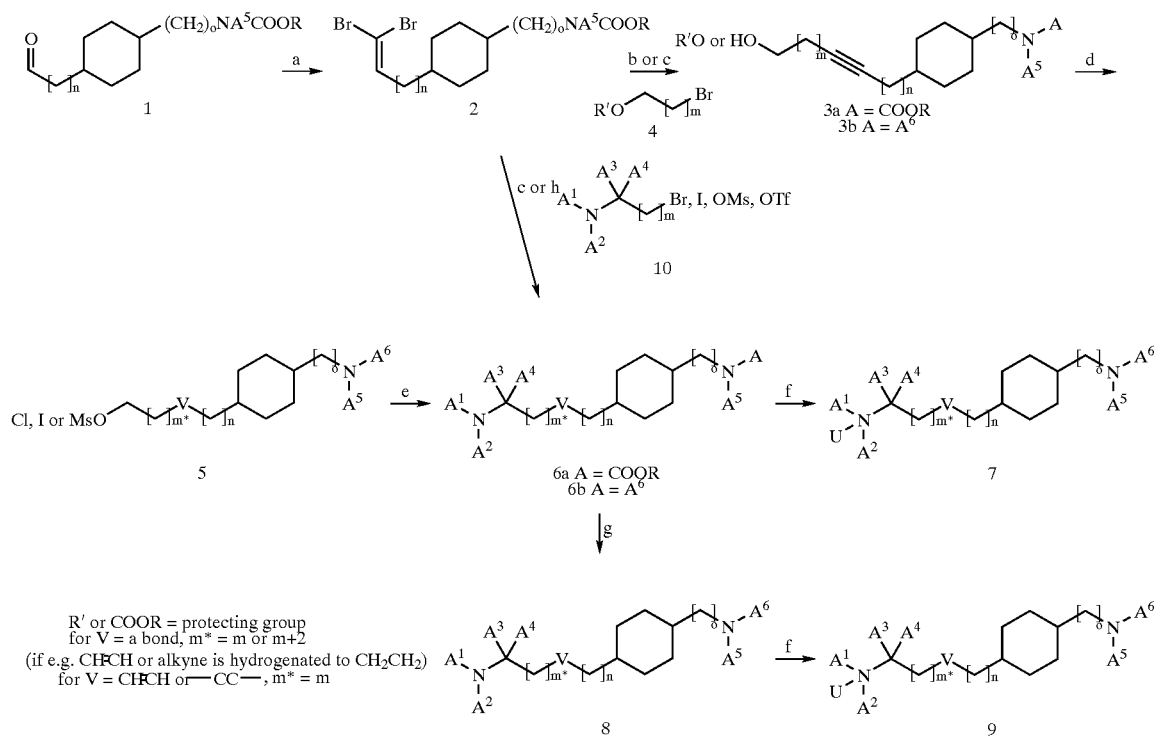

Scheme 7

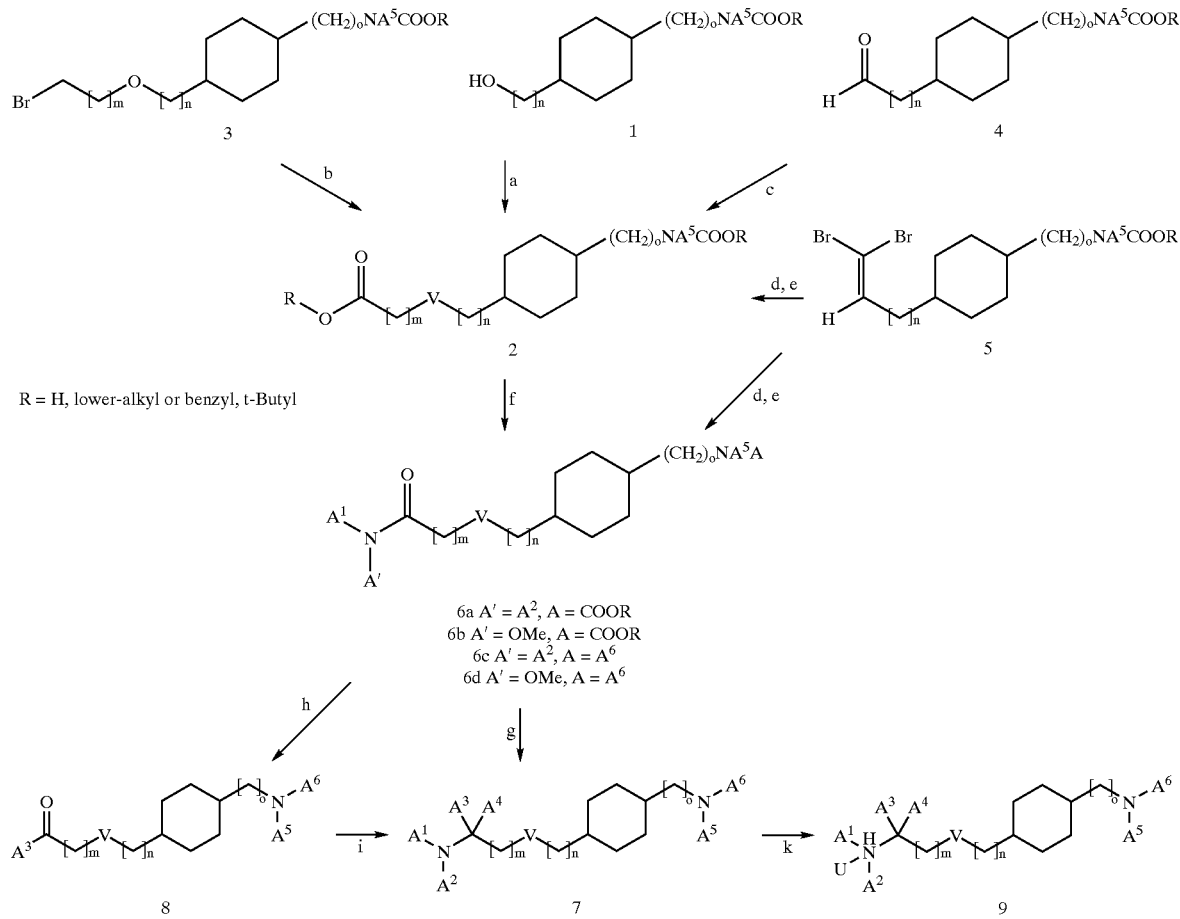

R = H, lower-alkyl or benzyl, t-Butyl

6a A' = A², A = COOR
6b A' = OMe, A = COOR
6c A' = A², A = A⁶
6d A' = OMe, A = A⁶

Scheme 1:

Scheme 1 to scheme 4 describe the synthesis of intermediates. Cis- or trans-(4-methylaminomethyl-cyclohexyl)-methanol ($A^5$=Me) 2 can be obtained from cis- or trans-(4-hydroxymethyl-cyclohexylmethyl)-carbamic acid tert-butyl ester 1 [U.S. (1998) U.S. Pat. No. 5,843,973 or U.S. (2000) U.S. Pat. No. 6,022,969 A] by treatment with lithium aluminium hydride in tetrahydrofuran between room temperature and the reflux temperature of the tetrahydrofuran (step a). Introduction of a tert-butoxycarbonyl protective function by treatment with di-tert-butyl-dicarbonate in methanol/triethylamine between −10° C. and room temperature gives compound 3 ($A^5$=Me) (step b). Compound 1 can also be first O-protected and then N-alkylated at the tert-butoxycarbonyl protected amino function with an alkyl or alkenyl halide in the presence of a base like sodium hydride in a solvent like N,N-dimethylformamide or acetonitrile at temperatures between room temperature and 80° C. to introduce substituents $A^5$; after O-deprotection the compound 3 is obtained. Compound 3 is subsequently oxidized to the corresponding aldehyde 4 by using e.g. Swern conditions: oxalyl chloride/dimethylsulfoxide/triethylamine in dichloromethane, −78° C. to room temperature (step c).

Scheme 2:

Cis or trans-[4-(Tert-butyl-dimethyl-silanyloxymethyl)-cyclohexyl]-methanol 1 is prepared from the corresponding bis-hydroxymethyl cyclohexane derivatives by treatment with one equivalent of n-butyl lithium in tetrahydrofuran at −78° C. followed by one equivalent of tert-butyl-dimethyl-chlorosilane at −65° C. to room temperature. Mesylation of [4-(tert-butyl-dimethyl-silanyloxymethyl)-cyclohexyl]-methanol 1 (methanesulfonyl chloride in dichloromethane and triethylamine at 0–10° C.) gives the corresponding methanesulfonate, which is treated with sodium cyanide in N,N-dimethylformamide at 80° C. to give the cyano compound 2 (step a). Direct reduction of the cyano compound 2 e.g. by hydrogenation with a platinum catalyst in acidic methanol gives the primary O-deprotected amine 3 (step b). Treatment of the amino-alcohol 3 first with di-tert-butyl-dicarbonate in dichloromethane in the presence of triethylamine followed by acetic anhydride and pyridine in dichloromethane gives the di-protected compound 4 (step c). Compound 4 can be N-alkylated at the primary tert-butoxycarbonyl protected amino function with an alkyl halide in the presence of a base like sodium hydride in a solvent like N,N-dimethylformamide or acetonitril at temperatures between room temperature and 80° C. to introduce substituents $A^5$ and give, after basic cleavage of the acetate function, the primary hydroxy compound 5 (step d). The primary hydroxy compound 5 can be oxidized subsequently to the corresponding aldehyde 6 by using e.g. Swern conditions:

oxalyl chloride/dimethylsulfoxide/triethylamine in dichloromethane, −78° C. to room temperature (step e).

Scheme 3:

Scheme 3 describes the synthesis of pure trans-aldehyde building block 8. Optionally $A^5$ substituted cyclohexanol 1 is synthesized by hydrogenation of the corresponding 4-aminophenol, 4-hydroxybenzylamine or tyramine. Amine 1 is converted to the N-protected-derivative 2 (e.g. ZCl, $Na_2CO_3$/THF/$H_2O$) (step a). Oxidation with TEMPO (2,2,6,6-Tetramethylpiperidine 1-oxyl, radical) and sodium hypochlorite gives ketone 3 (step b). Wittig reaction with (methoxymethyl)triphenylphosphonium chloride 4 in THF and potassium t-butoxide as base gives enolether 5 (step c). $A^5$-introduction is possible on this stage (with $A^5$-halogenide/NaH in DMF or DMA). Hydrolyses of enolether 5 with 1 N HCl in THF at reflux (step d) gives aldehyde 6. The crude aldehyde 6 (as a cis/trans mixture) can be isomerised via bisulfite-adduct 7 (with disodium pyrosulfite in water/TBME, step e). Bisulfite adduct 7 can then be converted to the pure trans-aldehyde 8 with aqueous $Na_2CO_3$ in water/TBME (step f).

Scheme 4:

The preparation of the starting materials for cyclohexyl derivatives of formula (I) in which V is a single bond, O, S, —CH═CH—CH$_2$—O—, —CH═CH—, or —C≡C—, is depicted in scheme 4. For compounds with n=0, the synthesis starts from cyclohexanol 1 which is converted to the Z-derivative or the BOC derivative 2 e.g. ZCl, $Na_2CO_3$, THF, $H_2O$ or -(BOC)$_2$O, iPrOH, $CH_2Cl_2$, respectively (step a). Optionally $A^5$ can be introduced in two ways. Lithium aluminum hydride reduction yields methylamino derivative which is e.g. BOC-protected to yield compounds 3. Compound 2 can also be first O-protected and then N-alkylated at the tert-butoxycarbonyl protected amino function with an $A^5$-halide in the presence of a base like sodium hydride in a solvent like N,N-dimethylformamide or acetonitrile at temperatures between room temperature and 80° C. to introduce substituents $A^5$; after O-deprotection compound 3 is obtained (step b) and then transferred into the desired $A^6$-derivative 4b (step c).

Reaction of Step c may be Performed in Two Steps:

First step: If necessary, introduction of the HOCH$_2$(CH$_2$)$_m$V-Spacer (V═O or CH═CHCH$_2$O) with phase transfer conditions (e.g. α,ω-dihaloalkanes or α,ω-dihaloalkenes, NaOH, nBu$_4$NHSO$_4$) yields the corresponding halogenide, which is hydrolyzed to the alcohol (e.g. with aqueous NaOH in THF or DMA). Alternatively the R" protected R"OCH$_2$(CH$_2$)$_m$V-Spacer can be introduced with in situ generation of the R"OCH$_2$(CH$_2$)$_m$O-triflate (from the corresponding R"O-alkanol with trifluoromethansulfonic anhydride/2,6-di-tert-butylpyridine in CH$_2$Cl$_2$ at 0° C.). This triflate is then reacted with alcohol 3 with 2,6-di-tert-butylpyridine as base in nitromethane at RT to 60° C. to yield R"OCH$_2$(CH$_2$)$_m$V-elongated 3 [following a procedure of Belostotskii, Anatoly M.; Hassner, Alfred. Synthetic methods. 41. Etherification of hydroxysteroids via triflates. Tetrahedron Lett. (1994), 35(28), 5075–6]. These R"OCH$_2$(CH$_2$)$_m$V-elongated 3 are completely O- and N-deprotected (e.g. for R"=Bzl, with Pd/C and H$_2$ in EtOH or MeOH/AcOH and for NA$^5$COOtBu with TFA in CH$_2$Cl$_2$ to give 4a).

Second step: Heteroaryl $A^6$-introduction to give 4b can be done with different conditions: Method A: Reaction of compound 4a with 2-Halo-heteroaryl/N-ethyldiisopropylamine 1 h to 5 days at 80 to 120° C. in DMA or no solvent, or Method B (for less reactive compounds): Reaction of compound 4a with 2-Halo-heteroaryl/N-ethyldiisopropylamine/CuI or NaI for 1–10 h at 120° C. or with microwave heating for 0.5 to 6 h at 120–150° C. in DMA.

For n=0, the starting material is cyclohexane-carboxylic acid 5 which is commercially available or van be synthesized (e.g. from aldehyde 6 by oxidation, scheme 3). Acid 5 is converted to the derivative 6 by ester formation (e.g. carbonyl-di-imidazole, methanol in THF) and optionally $A^5$-alkylated using sodium hydride and a reactive alkyl or alkenyl derivative (step d). Reduction with lithium aluminum hydride yields the N-protected alcohol 7 which can be transformed to 4b (step f) as described for 3 to 4b.

For n=1, the starting material is cyclohexyl acetic acid 5 (can be derived from 4-nitrophenylacetic acid according to Karpavichyus, K. I.; Palaima, A. I.; Knunyants, I. L.; BACCAT; Bull. Acad. Sci. USSR Div. Chem. Sci. (Engl. Transl.); EN; 29; 1980; 1689–1694; IASKA6; Izv. Akad. Nauk SSSR Ser. Khim.; RU; 10; 1980; 2374–2379 or T. P. Johnston et al. Journal of Medicinal Chemistry, 1977, Vol, No. 2, 279–290.) which can be converted to the corresponding alcohol following the protocol for the compounds 5 to 4b. Alternatively cyclohexyl acetic acid 5 can be synthesized (e.g. from ketone 3 scheme 3; via $C_2$-elongation by Horner-Emmons reaction with triethyl phosphono acetate, sodium alcoholate) and protected as discussed before.

For n>=2, the starting material is cyclohexane-carboxylic acid 5. Acid chain elongation (n>1) can be achieved using methods known in the art or as described below:

For $C_2$-elongation: Swern oxidation of the alcohol 7 to the corresponding aldehyde followed by Horner-Emmons reaction with triethyl phosphono acetate, sodium alcoholate in an alcohol gives the unsaturated ester 8 (step g). This can be subjected to hydrogenation with 10% palladium on carbon in methanol and reduction with lithium aluminum hydride in THF to yield the chain-elongated alcohol which can be transformed to 4b (step h) as described for 3 to 4b. The sequence 7→8 can be repeated to get the further $C_2$-elongated compounds 1f desired.

For $C_{(m)}$-elongation, Corey-Fuchs methodology may be used: Therefore, acid 5 is converted to the Weinreb derivative by treatment with N,O-dimethyl-hydroxyl-amine.hydrochloride with EDCI and HOBT in CH$_2$Cl$_2$ at room temperature, $A^5$ alkylated ($A^5$-halogenide with NaH in DMF or DMA at 0° C. to RT) and reduced by lithium aluminum hydride to the corresponding aldehyde 9 (step i). This aldehyde 9 can be treated with triphenylphosphine, tetrabromomethane and triethylamine in CH$_2$Cl$_2$ at 0° C. to RT to yield 2,2-Dibromo-vinyl derivative 10. Rearrangement with n-BuLi (ca 1.6 M in hexane) in THF at −78° C., followed by reaction with formaldehyde (−78° C. to RT) gives the propargyl alcohol 12 [step 1, following conditions described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21.]. For longer side chains, the rearrangement is performed with n-BuLi (ca 1.6 M in hexane) in THF at −78° C. as described above, followed by addition of a cosolvens such as DMPU and reaction with O-protected 1-bromo-alcohols 11 (step m) to give the O-protected compounds 12.

O-deprotection (if necessary) and N-deprotection of 12 followed by reaction with the 2-Halo-heteroaryl, as described before (step n), yields derivatives 4b (V═—C≡C—). For V═—CH═CH— or single bond, hydrogenation of 12 e.g with Raney-Ni, 10% Pd/C or PtO$_2$.H$_2$O/H$_2$ (step o) and reaction of compound 13 with the 2-Haloheteroaryl, as described before (step n), yields derivatives 4b.

Finally, the substitution pattern for $A^6$ in product 4b can be manipulated: e.g. by Suzuki reactions if $A^6$ is a Haloheteroaryl or by nucleophilic displacements, e.g. if $A^6$ is 6-Chloro-pyridazine, reaction with sodium alcoholate in DMA at 80° C. gives the alkoxy substituted compound.

Scheme 5:

The synthesis of ether (V=O and S) derivatives of formula (I) is depicted in scheme 5. For the preparation of derivatives with n=0, the cyclohexanol derivative 1 (synthesis see scheme 1–4) can be treated under phase transfer conditions e.g. α,ω-dihaloalkanes or α,ω-dihaloalkenes, NaOH, $nBu_4NHSO_4$ to yield bromide 2. For n>0, alcohol derivative 1 may be treated with α,ω-dihaloalkane (for $C_4$ or longer alkanes) in the presence of NaH in DMF 0° C. to RT to yield bromide 2. For shorter alkanes the method of choice is the in situ generation of the haloalkane-triflate (from the corresponding haloalkanol with trifluoromethansulfonic anhydride/2,6-di-tert-butylpyridine in $CH_2Cl_2$ at 0° C.). This haloalkane-triflate is then reacted with alcohol 1 with 2,6-di-tert-butylpyridine as base in nitromethane at RT to 60° C. to yield bromide 2 [following a procedure of Belostotskii, Anatoly M.; Hassner, Alfred. Synthetic methods. 41. Etherification of hydroxysteroids via triflates. Tetrahedron Lett. (1994), 35(28), 5075–6].

Amination of bromide 2 with amine $A^1A^2NH$ in DMA or DMF, at RT or in MeOH at RT to reflux yields the final amine 3, optionally DBU may be added and NaI. In case $A^1$ or $A^2$ is a H, the second substitutent can be introduced in a second step, e.g. N-methylation with $NaH_2PO_3$/formaldehyde. Amine 3 may be converted to a salt or to the N-oxide 4 using a mixture of hydrogen peroxide urea adduct and phthalic anhydride in $CH_2Cl_2$ at RT.

Alternatively, the alcohol 1 can be converted to the amine 5 by attaching the pre-assembled fragment $A^1A^2NC(A^3A^4)(CH_2)_m$—VH (V=O and S), which can be synthesized by known methods, to the mesylate/halogenate of derivative 1 using alkylating conditions (step d). Alternatively, fragment $A^1A^2NC(A^3A^4)(CH_2)_m$—OH can also be mesylated/halogenated and reacted with derivative 1 using alkylating conditions (step d). The amine 5 can be converted to its salt or the N-oxide 6 as described above (step c).

Finally, the substitution pattern for $A^6$ in product 5 can be manipulated: e.g. hydrolysis of a N-acetyl group to an $NH_2$ or by Suzuki reactions if $A^6$ is a Halo-heteroaryl or by nucleophilic displacements, e.g. if $A^6$ is 6-Chloro-pyridazine, reaction with sodium alcoholate in DMA at 80° C. gives the alkoxy substituted compound.

Furthermore the substitution pattern of $A^1$ or $A^2$ may be modified, e.g. treatment of hydroxyethylamine with DAST.

Scheme 6:

In scheme 6 the synthesis of C-analogues cyclohexanes of the general structure I in which V is a single bond, —CH=CH— or —C≡C— is described. The synthesis starts from aldehyde 1 which is described in scheme 1–4. Side chain extension is effected through application of the Corey-Fuchs method. The aldehyde 1 is treated with triphenylphosphine, tetra-bromo-methane and triethylamine in $CH_2Cl_2$ at 0° C. to RT to yield 2,2-Dibromo-vinyl derivative 2. Rearrangement with n-BuLi (ca 1.6 M in hexane) in THF at –78° C., followed by reaction with formaldehyde (–78° C. to RT; step b) leads to the propargyl alcohol 3a [following conditions described in: Marshall, James A.; Bartley, Gary S.; Wallace, Eli M. Total Synthesis of the Pseudopterane (–)-Kallolide B, the Enantiomer of Natural (+)-Kallolide B. J. Org. Chem. (1996), 61(17), 5729–5735; and Baker, Raymond; Boyes, Alastair L.; Swain, Christopher J. Synthesis of talaromycins A, B, C, and E. J. Chem. Soc., Perkin Trans. 1 (1990), (5), 1415–21.]. BOC-deprotection (TFA, $CH_2Cl_2$) followed by treatment with $A^6$-heteroaryl as described before (scheme 4) gives compounds of the formula 3b.

For longer side chains, the rearrangement of dibromoalkene 2 is performed with n-BuLi (ca 1.6 M in hexane) in THF at –78° C. as above, followed by addition of a cosolvens such as DMPU and reaction with O-protected 1-bromoalcohols 4 to yield the O-protected compounds 3a which can be deprotected to the corresponding alkynol 3a derivative in MeOH at 50–60° C. in the presence of catalytic amount of pyridinium toluene-4-sulfonate. BOC-deprotection (TFA, $CH_2Cl_2$) followed by treatment with $A^6$-heteroaryl as described before (scheme 4) gives compounds of the formula 3b (step c).

Mesylation of alcohol 3b with methanesulfonylchloride, pyridine or lutidine with or without DMAP in $CH_2Cl_2$ at 0° C. to RT yields mesylate/chloride or pyridinium derivative 5 which can be converted to the amine 6b in DMA or MeOH at RT or at 50–70° C. with an excess of the corresponding amine $NHA^1A^2$ (step e). In case $A^1$ or $A^2$ is a H, the second substitutent can be introduced in a second step, e.g. N-methylation with $NaH_2PO_3$/formaldehyde.

To obtain compounds 6b in which $A^3$ and/or $A^4$ is not H and m>0, compounds 2 can be reacted with compounds 10 under the same condition as described for step c. The building blocks 10 can be prepared by known methods.

For the introduction of the group $(A^1,A^2)N$—$C(A^3,A^4)$- wherein $A^3$ and/or $A^4$ is not H and m=0, a two step procedure has to be followed: first the rearrangement dibromide 2 with n-BuLi (ca 1.6 M in hexane) in THF at –78° C., followed by reaction with the corresponding aldehyde ($A^3$ or $A^4$-COH) or ketone ($A^3COA^4$, at –78° C. to RT) leading to the $A^3,A^4$ substituted propargyl alcohol which can be transformed to a phosphorester [see: Bartlett, Paul A.; McQuaid, Loretta A. Total synthesis of (±)-methyl shikimate and (±)-3-phosphoshikimic acid. J. Am. Chem. Soc. (1984), 106(25), 7854–60] and reacted with the desired $(A^1,A^2)$-amine in the presence of Tetrakis(triphenylphosphine)palladium in THF to yield the desired $A^3,A^4$-substituted compound 6a (step h). BOC-deprotection (TFA, $CH_2Cl_2$) followed by treatment with $A^6$-heteroaryl as described before (scheme 4) gives compounds of the formula 6b.

Compounds in which V is a single bond or —CH=CH— can be obtained by hydrogenation of compound 6b with $PtO_2.H_2O/H_2$ (yields the saturated analogue 8) or by hydrogenation with other known methods (e.g. Raney-Ni, yields the double bond analogue 8). Alternatively, the alkyne group can already be reduced at an earlier stage e.g. alcohol 3a (e.g. LAH-reduction for m=0, gives V=trans-CH=CH— or hydrogenation with Pt/C or $PtO_2.H_2O$ yields V=$CH_2CH_2$— (single bond respectively)), and the resulting compound can then be transformed further to the final compounds 8 and/or 9.

Finally, the substitution pattern for $A^6$ in product 6b or 8 can be manipulated: e.g. hydrolysis of a N-acetyl group to an $NH_2$ or by Suzuki reactions if $A^6$ is a Halo-heteroaryl or by nucleophilic displacements, e.g. if $A^6$ is 6-Chloro-pyridazine, reaction with sodium alcoholate in DMA at 80° C. gives the alkoxy substituted compound.

Furthermore the substitution pattern of $A^1$ or $A^2$ may be modified, e.g. treatment of hydroxyethylamine with DAST.

In case $A^1$ or $A^2$ is a H, the second substitutent can be introduced in a second step, e.g. N-methylation with $NaH_2PO_3$/formaldehyde.

The amines 6b and 8 can be converted to a salt or as described in step f to the N-oxide 7 and 9, respectively, using a mixture of hydrogen peroxide urea adduct and phthalic anhydride in $CH_2Cl_2$ at RT.

Scheme 7:

Another possible approach for the introduction of the substituted side chain is depicted in scheme 7. The synthesis of the main intermediate 2 begins by attaching an ω-hydroxyalkylcarbonic acid ester to alcohol 1 via the in situ generated triflate in analogy to Belostotskii, Anatoly M.; Hassner, Alfred. Synthetic methods. 41. Etherification of hydroxysteroids via triflates. Tetrahedron Lett. (1994), 35(28), 5075–6 (step a). Alternatively, the ester 2 can be prepared from the bromide 3 (synthesis described in scheme 5) by treatment with e.g. acetocyanhydrine in acetonitrile, followed by a Pinner reaction and hydrolysis of the imidate to the corresponding ester (step b).

For V=CH=CH, the ester 2 or its corresponding acid may be prepared from aldehyde 4 (synthesis described in scheme 1–4) by treatment with the corresponding Wittig reagent $Ph_3P(CH_2)_{m+1}CO_2R/H$. For V=a bond, hydrogenation of the Wittig product under standard conditions yields the saturated product 2.

For V=—C≡C—, ester 2 or amide 6a may be derived from the dibromoderivative 5 (synthesis according to scheme 4) by rearrangement with n-BuLi (ca 1.6 M in hexane) in THF at −78° C., followed by reaction with chloroformate (->2) or dialkylcarbamoyl chloride (->6a) (−78° C. to RT; step d). For longer side chains, the rearrangement of dibromoalkene 5 may be performed with n-BuLi (ca 1.6 M in hexane) in THF at −78° C. as above, followed by addition of a cosolvens such as DMPU and reaction with a suitable protected 1-bromo-alkylalcohol Br-$(CH_2)_mCH_2OH$, followed by oxidation to yield the compound 2 as acid (step e).

Saponification of the ester 2 using standard conditions e.g. LiOH in EtOH, MeOH or THF, followed by treatment with $NHA^1A^2$ or $NHA^1A'$, EDCI, HOBT and a base such as Huenig's base, $NEt_3$, NMM in $CH_2Cl_2$, DMF, DMA or dioxane gives amide 6a or 6b. N-deprotection of 6a or 6b followed by reaction with the 2-Halo-heteroaryl, as described in scheme 4 yields derivatives 6c and 6d.

Amide 6c can be transferred to amine 7 ($A^3, A^4$=Me) by reaction with methylmagnesium bromide, $ZrCl_4$ in THF at low temperature (see Stephen M. Denton, Anthony Wood, A Modified Bouveault Reaction for the Preparation of α,α-dimethylamines from Amides, Synlett 1999,1, 55–56.) or by treatment with other grignard reagents in the presence of $ZrCl_4$ or $Ti(OiPr)_4$ (see V. Chalinski, A. de Meijere, A versatile New Preparation of Cyclopropylamines from acid dialkylamides, Angew. Chem. Int. Ed. Engl. 1996, 35, No4, 413–4.).

For $A^1$=Me, A'=OMe, amide 6d can be treated with a grignard reagent $A^3MgX$ to give the corresponding ketone 8. Reductive alkylation of the ketone 8 by treatment with $NHA^1A^2$ in the presence of tetraisopropyl orthotitanate, followed by reduction with $NaCNBH_3$ in ethanol yields the amine 7 (see: R. J. Mattson, K. M. Pham, D. J. Leuck, K. A. Cowen, J. O. C. 1990, 55, 2552–4.).

Finally, the substitution pattern for $A^6$ in product 7 can be manipulated: e.g. hydrolysis of a N-acetyl group to an $NH_2$ or by Suzuki reactions if $A^6$ is a Halo-heteroaryl or by nucleophilic displacements, e.g. if $A^6$ is 6-Chloro-pyridazine, reaction with sodium alcoholate in DMA at 80° C. gives the alkoxy substituted compound.

Furthermore the substitution pattern of $A^1$ or $A^2$ may be modified, e.g. treatment of hydroxyethylamine with DAST. In case $A^1$ or $A^2$ is a H, the second substitutent can be introduced in a second step, e.g. N-methylation with $NaH_2PO_3$/formaldehyde.

Amine 7 may be converted to a salt or to the N-oxide 9 using a mixture of hydrogen peroxide urea adduct and phthalic anhydride in $CH_2Cl_2$ at RT.

Pure cis- or trans-aminocyclohexane derivatives can be obtained either by separation of the mixtures using HPLC or by using stereochemically defined starting materials.

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/μl with ethanol and mixed with phosphate buffer-1% BSA (bovine serum albumin). A stock solution of 1 mM test substance in DMSO was diluted to the desired concentration with phosphate buffer-1% BSA. 40 μl of microsomes were mixed with 20 μl of the solution of the test substance and the reaction was subsequently started with 20 μl of the [$^{14}$C] R,S-MOS solution. The final conditions were: 0.4 mg/ml of microsomal proteins and 30 μl of [$^{14}$C]R,S-MOS in phosphate buffer, pH 7.4, containing 0.5% albumin, DMSO <0.1% and ethanol <2%, in a total volume of 80 μl.

After 1 hour at 37° C. the reaction was stopped by the addition of 0.6 ml of 10% KOH-methanol, 0.7 ml of water and 0.1 ml of hexane:ether (1:1, v/v) which contained 25 μg of non-radioactive MOS and 25 μg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 μl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the $IC_{50}$ value was calculated, i.e. the concentration required to reduce the conversion of MOS into lanosterol to 50% of the control value. The preferred compounds of the present invention exhibit $IC_{50}$ values of 1 nM to 10 μM, preferably of 1–100 nM.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations:

AcOH=Acetic acid, BOC=t-Butyloxycarbonyl, BuLi=Butyllithium, $CH_2Cl_2$=dichloromethane, DAST=Diethylamino-sulfurtrifluoride, DEAD=Diethyl azodicarboxylate, DBU=1,8-Diazabicyclo[5.4.0]undec-7-ene(1,5-5), DIBALH=Di-1-butylaluminium hydride, DMA N,N-Dimethylacetamide, DMAP=4-Dimethylaminopyridine, DMF=N,N-Dimethylformamide, DMPU=1,3-Dimethyl-3,4,5,6-tetrahydro-2(1H)-pyrimidinone, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HOBT=1-Hydroxybenzo-triazole, Huenig's base=$iPr_2NEt$=N-Ethyl diisopropylamine, LAH=Lithium aluminium hydride, LDA=Lithium diisopropylamide, $LiBH_4$=Lithium borohydride, MeOH=Methanol, NaI=Sodium iodide, $PdCl_2(dppf)$=(1,1'-Bis(diphenylphosphino)ferrocene)dichloro-palladium(II).$CH_2Cl_2$ (1:1), $Pd(Ph_3P)_4$=Tetrakis(triphenylphosphine)palladium, Red-Al=Sodium bis(2-methoxyethoxy) aluminium hydride, TEMPO=2,2,6,6-Tetramethylpiperidine 1-oxyl, radical, TBDMSCl=t-Butyldimethylsilyl chloride, TBME=t-Butyl methyl ether, TFA=Trifluoroacetic acid, THF=Tetrahydrofurane, quant=quantitative.

General Remarks

All reactions were performed under argon.

Example 1

1.1

A solution of 20 g (82.2 mmol) trans-4-tert-Butoxycarbonylamino-cyclohexanecarboxylic acid in 1.2 l $CH_2Cl_2$ was treated with 12.83 g (131.5 mmol) N,O-dimethylhydroxylamine hydrochloride, 10.85 ml (98.6 mmol) N-methylmorpholine and at 0° C. with 18.91 g (98.64 mmol) EDCI and 12.62 g (82.2 mmol) HOBT. The reaction mixture was stirred 2 h at room temperature and extracted with aqueous 10% $KHSO_4/Et_2O$ (3×). The organic phases were washed with aqueous saturated $NaHCO_3$, 10% NaCl and dried over $Na_2SO_4$ to yield 24.25 g (quantitative) of trans-[4-(Methoxy-methyl-carbamoyl)-cyclohexyl]-carbamic acid tert-butyl ester, mp: 130–140° C., slowly dec.; MS: 287 ($MH^+$).

1.2

A solution of 24.18 g (82 mmol) of trans-[4-(Methoxy-methyl-carbamoyl)-cyclohexyl]-carbamic acid tert-butyl ester in 80 ml of DMF was treated at 0° C. with 5.37 g (123 mmol) of NaH (55% in oil) in small portions. The reaction was stirred for 1 h at 0° C., then treated slowly (20 min) with 40.9 ml (656 mmol) iodomethane and warmed up to RT over night. The reaction was cooled and neutralized with aqueous 10% $KHSO_4$ and poured into water/$Et_2O$ (3×). The organic phase was washed with aqueous 10% NaCl, dried over $Na_2SO_4$ evaporated and purified by flash silica gel column ($CH_2Cl_2$/EtOAc 9:1 to 1:1) to yield 20.69 g (84%) of trans-[4-(Methoxy-methyl-carbamoyl)-cyclohexyl]-methyl-carbamic acid tert-butyl ester, MS: 301 ($MH^+$).

1.3

A solution of 2.09 g (55 mmol) LAH in 250 ml THF was cooled (−50° C.) and treated during 25 min with a solution of 15.02 g (50 mmol) of trans-[4-(Methoxy-methyl-carbamoyl)-cyclohexyl]-methyl-carbamic acid tert-butyl ester in 250 ml THF. The reaction was warmed up to +15° C. for 3.5 h, cooled (−78° C.) and hydrolyzed with a suspension of 15 g $MgSO_4.7H_2O$, 15 g silicagel in 50 ml aqueous 10% $KHSO_4$. The cooling bath was removed, THF was added, the mixture was stirred for 30 min and filtered. After evaporation, the residue was dissolved in $CH_2Cl_2$, dried over $Na_2SO_4$ and evaporated to yield 12.83 (quantitative) of trans-(4-Formyl-cyclohexyl)-methyl-carbamic acid tert-butyl ester, MS: 241 (M).

1.4

A solution of 52.45 g (200 mmol) triphenylphosphine in 200 ml $CH_2Cl_2$ was treated with 33.16 g (100 mmol) tetrabromomethane (the reaction heated up to reflux) and after 50 min with 32.06 ml (230 mmol) triethylamine (the reaction heated up to reflux and became dark violet). After cooling (0° C.), 12.83 g (50 mmol) of trans-(4-Formyl-cyclohexyl)-methyl-carbamic acid tert-butyl ester in 125 ml $CH_2Cl_2$ were added during 10 min. The solution was stirred for 16 h at RT, evaporated and filtered through silica gel (deactivated with hexane/0.5% $Et_3N$) with hexane and then hexane/$Et_2O$ 4:1 to 1:1 as eluent to yield 13.28 g (67%) of trans-[4-(2,2-Dibromo-vinyl)-cyclohexyl]-methyl-carbamic acid tert-butyl ester, mp: 93–99° C., dec.; MS: 396 ($MH^+$, 2Br).

1.5

The following reaction was performed in analogy to the reaction described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735 and Baker, Raymond; Boyes, Alastair L.; Swain, Christopher J. Synthesis of talaromycins A, B, C, and E. J. Chem. Soc., Perkin Trans. 1 (1990), (5), 1415–21.). A solution of 993 mg (2.5 mmol) of trans-[4-(2,2-Dibromo-vinyl)-cyclohexyl]-methyl-carbamic acid tert-butyl ester in 20 ml THF was treated at −78° C. with 3.28 ml (5.25 mmol) of BuLi (ca 1.6 M in hexane). After 2 h at this temperature 790 mg (25 mmol) of paraformaldehyde were added. The reaction mixture was warmed up to RT for 3 h and after 1 h at this temperature extracted with water/$Et_2O$ (3×). The organic phases were washed with aqueous 10% NaCl, dried over $Na_2SO_4$ and evaporated. Purification by flash-chromatography on silica gel (hexane/EtOAc 4:1) yielded 530 mg (79%) of trans-[4-(3-Hydroxy-prop-1-ynyl)-cyclohexyl]-methyl-carbamic acid tert-butyl ester, MS: 268 ($MH^+$).

1.6

A solution of 9.0 g (33.66 mmol) of trans-[4-(3-Hydroxy-prop-1-ynyl)-cyclohexyl]-methyl-carbamic acid tert-butyl ester in 185 ml $CH_2Cl_2$ was treated at 0° C. with 136 ml of TFA (for 30 min). After 15 min at this temperature, the reaction was evaporated, treated with cold (0° C.) 1 N NaOH (saturated with NaCl) and extracted with $CH_2Cl_2$/MeOH 9:1 (3×). The organic phase was dried over $Na_2SO_4$ and evaporated to yield 5.84 g (quantitative) of trans-3-(4-Methylamino-cyclohexyl)-prop-2-yn-1-ol, MS: 167 (M).

1.7

A mixture of 0.51 g (3.05 mmol) trans-3-(4-Methylamino-cyclohexyl)-prop-2-yn-1-ol, 0.87 g (3.66 mmol) 2,5-dibromo-pyrimidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] and 1.78 ml (10.34 mmol) N-ethyldiisopropylamine was heated for 2.5 h at 80° C. The reaction was cooled, evaporated and partitioned between aqueous saturated $NaHCO_3$/$Et_2O$ (3×). The organic phases were washed with aqueous 10% NaCl, dried ($NaSO_4$) and evaporated. Flash chromatography on silica gel (hexane/EtOAc 95:5) gave 0.72 g (73%) of trans-3-{4-[(5-Bromo-pyrimidin-2-yl)-methyl-amino]-cyclohexyl}-prop-2-yn-1-ol, mp: 156–157° C.; MS: 324 ($MH^+$, 1Br).

1.8

In analogy to example 1.7, trans-3-(4-Methylamino-cyclohexyl)-prop-2-yn-1-ol and 3.2 equivalent of 2-chloropyrimidine gave after 3 h at 80° C. trans-3-[4-(Methyl-pyrimidin-2-yl-amino)-cyclohexyl]-prop-2-yn-1-ol, mp: 138–140° C., dec.; MS: 245 (M).

1.9

In analogy to example 1.7, trans-3-(4-Methylamino-cyclohexyl)-prop-2-yn-1-ol and 1.2 equivalent of 2-chloropyridine-5-carbonitrile gave after 29 h at 80° C. trans-6-{[4-(3-Hydroxy-prop-1-ynyl)-cyclohexyl]-methyl-amino}-nicotinonitrile, mp: 126.1–127.4; MS: 270 ($MH^+$).

1.10

In analogy to example 1.7, trans-3-(4-Methylamino-cyclohexyl)-prop-2-yn-1-ol and 1.5 equivalent of 2-Bromo-5-chloro-pyrimidine [synthesized from 5-chloro-2-hydroxypyrimidine in analogy to Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] were heated for 0.5 h at 80° C., 1 h at 120° C., then 0.5 equivalent of 2-Bromo-5-chloro-pyrimidine were added and heated for 1 h at 120° C. to give after work up trans-3-{4-[(5-Chloro-pyrimidin-2-yl)-methyl-amino]-cyclohexyl}-prop-2-yn-1-ol, mp: 148–150° C., dec.; MS: 280 ($MH^+$, 1Cl).

1.11

A mixture of 0.67 g (4 mmol) trans-3-(4-Methylamino-cyclohexyl)-prop-2-yn-1-ol, 2.76 g (18 mmol) of 3,6-dichloropyridazine and 1.76 ml (13.6 mmol) N-ethyldiisopropylamine was heated for 3.5 h at 80° C., diluted with 1 ml DMF and heated for 4 days at 80° C. and one day at 120° C. The reaction was cooled, evaporated and partitioned between aqueous saturated $NaHCO_3$/$Et_2O$ (3×). The organic phases were washed with aqueous 10% NaCl, dried ($NaSO_4$) and evaporated. Flash chromatography on silica gel ($MeCl_2$/$Et_2O$ 95:5 to 9:1) gave 0.61 g (54%) of trans-3-{4-[(6-Chloro-pyridazin-3-yl)-methyl-amino]-cyclohexyl}-prop-2-yn-1-ol, MS: 280 ($MH^+$, 1Cl).

1.12

A mixture of 0.67 g (4 mmol) trans-3-(4-Methylamino-cyclohexyl)-prop-2-yn-1-ol, 1.24 ml (12 mmol) of 5-bromo-2-fluoropyridine and 1.76 ml (13.6 mmol) N-ethyldiisopropylamine was heated for 3 h at 80° C. and 24 h at 120° C. The mixture was diluted with 1 ml DMF, treated with a catalytic amount of NaI and heated for 2 days at 120° C. The reaction was cooled, evaporated and partitioned between aqueous saturated $NaHCO_3$/$Et_2O$ (3×). The organic phases were washed with aqueous 10% NaCl, dried ($NaSO_4$) and evaporated. Flash chromatography on silica gel ($MeCl_2$/$Et_2O$ 97.5:2.5 to 92.5:7.5) gave 0.57 g (44%) of trans-3-{4-[(5-Bromo-pyridin-2-yl)-methyl-amino]-cyclohexyl}-prop-2-yn-1-ol, MS: 323 ($MH^+$, 1Br).

1.13

In analogy to example 1.12, trans-3-(4-Methylamino-cyclohexyl)-prop-2-yn-1-ol and 2-fluoropyridine gave after 5 days at 120° C. trans-3-[4-(Methyl-pyridin-2-yl-amino)-cyclohexyl]-prop-2-yn-1-ol, MS: 245 ($MH^+$).

1.14

In analogy to example 1.12, trans-3-(4-Methylamino-cyclohexyl)-prop-2-yn-1-ol and 2-chloropyrazine gave trans-3-[4-(Methyl-pyrazin-2-yl-amino)-cyclohexyl]-prop-2-yn-1-ol, mp: 147–149° C., dec.; MS: 246 ($MH^+$).

1.15

A solution of 0.24 g (1.44 mmol) of trans-3-(4-Methylamino-cyclohexyl)-prop-2-yn-1-ol, 0.7 ml (5.74 mmol) of 2-chloro-5-ethylpyrimidine, 0.83 ml (4.88 mmol) N-ethyldiisopropylamine and a catalytic amount of NaI in 1.5 ml DMA was heated in the microwave oven for 3.75 h at 120° C. The reaction was cooled and partitioned between aqueous saturated NaHCO$_3$/Et$_2$O (3×). The organic phases were washed with aqueous 10% NaCl, dried (NaSO$_4$) and evaporated. Flash chromatography on silica gel (hexane/EtOAc 9:1 to 1:1) gave 0.24 g (61%) of trans-3-{4-[(5-Ethyl-pyrimidin-2-yl)-methyl-amino]-cyclohexyl}-prop-2-yn-1-ol, MS: 274 (MH$^+$).

1.16

In analogy to example 1.15, trans-3-(4-Methylamino-cyclohexyl)-prop-2-yn-1-ol and 3-chloro-6-methylpyridazine gave, with no NaI after 4 h at 150° C. and ¾h at 120° C. in the microwave oven, trans-3-{4-[Methyl-(6-methyl-pyridazin-3-yl)-amino]-cyclohexyl}-prop-2-yn-1-ol, MS: 260 (MH$^+$).

1.17

A solution of 420 mg (1.3 mmol) of trans-3-{4-[(5-Bromo-pyrimidin-2-yl)-methyl-amino]-cyclohexyl}-prop-2-yn-1-ol in 10 ml CH$_2$Cl$_2$ was treated at 0° C. with 0.11 ml (1.43 mmol) methanesulfonylchloride, 0.16 ml (1.95 mmol) pyridine and 159 mg (1.3 mmol) DMAP. The reaction was stirred for 3.5 h at room temperature, water (2 ml) was added and stirred for 5 min. After extraction with aqueous saturated NaHCO$_3$/Et$_2$O(3×), the organic phase was washed with aqueous 10% NaCl, dried over Na$_2$SO$_4$ and evaporated to yield 540 mg (quantitative) of trans-Methanesulfonic acid 3-{4-[(5-bromo-pyrimidin-2-yl)-methyl-amino]-cyclohexyl}-prop-2-ynyl ester, MS: 402 (MH$^+$, 1Br).

1.18

In analogy to example 1.17, trans-3-[4-(Methyl-pyrimidin-2-yl-amino)-cyclohexyl]-prop-2-yn-1-ol was converted to trans-Methanesulfonic acid 3-[4-(methyl-pyrimidin-2-yl-amino)-cyclohexyl]-prop-2-ynyl ester, MS: 402 (MH$^+$).

1.19

In analogy to example 1.17, trans-6-{[4-(3-Hydroxy-prop-1-ynyl)-cyclohexyl]-methyl-amino}-nicotinonitrile was converted to trans-Methanesulfonic acid 3-{4-[(5-cyano-pyridin-2-yl)-methyl-amino]-cyclohexyl}-prop-2-ynyl ester, MS: 348 (MH$^+$).

1.20

In analogy to example 1.17, trans-3-{4-[(5-Chloro-pyrimidin-2-yl)-methyl-amino]-cyclohexyl}-prop-2-yn-1-ol was converted to trans-Methanesulfonic acid 3-{4-[(5-chloro-pyrimidin-2-yl)-methyl-amino]-cyclohexyl}-prop-2-ynyl ester, MS: 357 (MH$^+$, 1Cl).

1.21

In analogy to example 1.17, trans-3-{4-[(6-Chloro-pyridazin-3-yl)-methyl-amino]-cyclohexyl}-prop-2-yn-1-ol was converted to trans-Methanesulfonic acid 3-{4-[(6-chloro-pyridazin-3-yl)-methyl-amino]-cyclohexyl}-prop-2-ynyl ester, MS: 358 (MH$^+$, 1Cl).

1.22

In analogy to example 1.17, trans-3-{4-[(5-Bromo-pyridin-2-yl)-methyl-amino]-cyclohexyl}-prop-2-yn-1-ol was converted to trans-Methanesulfonic acid 3-{4-[(5-bromo-pyridin-2-yl)-methyl-amino]-cyclohexyl}-prop-2-ynyl ester, MS: 401 (MH$^+$, 1Br).

1.23

In analogy to example 1.17, trans-3-[4-(Methyl-pyridin-2-yl-amino)-cyclohexyl]-prop-2-yn-1-ol was converted to trans-Methanesulfonic acid 3-[4-(methyl-pyridin-2-yl-amino)-cyclohexyl]-prop-2-ynyl ester, MS: 323 (MH$^+$).

1.24

In analogy to example 1.17, trans-3-[4-(Methyl-pyrazin-2-yl-amino)-cyclohexyl]-prop-2-yn-1-ol was converted to trans-Methanesulfonic acid 3-[4-(methyl-pyrazin-2-yl-amino)-cyclohexyl]-prop-2-ynyl ester, MS: 324 (MH$^+$).

1.25

In analogy to example 1.17, trans-3-{4-[(5-Ethyl-pyrimidin-2-yl)-methyl-amino]-cyclohexyl}-prop-2-yn-1-ol was converted to trans-1-(3-{4-[(5-Ethyl-pyrimidin-2-yl)-methyl-amino]-cyclohexyl}-prop-2-ynyl)-pyridinium; methanesulfonate, MS: 335 (MH$^+$).

1.26

A solution of 0.246 g (0.95 mmol) of trans-3-{4-[Methyl-(6-methyl-pyridazin-3-yl)-amino]-cyclohexyl}-prop-2-yn-1-ol in 7 ml CH$_2$Cl$_2$ was treated at 0° C. with 0.081 ml (1.04 mmol) methanesulfonylchloride and 0.17 ml (1.42 mmol) 2,6-lutidine. The reaction was stirred for 22 h at room temperature, water (1 ml) was added and stirred for 5 min. After extraction with aqueous saturated NaHCO$_3$/Et$_2$O(3×), the organic phase was washed with aqueous 10% NaCl, dried over Na$_2$SO$_4$ and evaporated to yield 0.285 g of crude trans-[4-(3-Chloro-prop-1-ynyl)-cyclohexyl]-methyl-(6-methyl-pyridazin-3-yl)-amine, MS: 278 (MH$^+$, 1Cl).

Example 2

A solution of 125 mg (corresponding to 0.30 mmol) of crude trans-Methanesulfonic acid 3-{4-[(5-bromo-pyrimidin-2-yl)-methyl-amino]-cyclohexyl}-prop-2-ynyl ester in 3 ml of methanol was cooled (0° C.), treated with 0.54 ml (3 mmol) of Dimethylamine (33% in EtOH 5.6M) and stirred for 20 h at RT. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 99:1 to 97.5:2.5) gave 65 mg (62%) of pure trans-(5-Bromo-pyrimidin-2-yl)-[4-(3-dimethylamino-prop-1-ynyl)-cyclohexyl]-methyl-amine, mp: 83–84° C., dec.; MS: 351 (MH$^+$, 1Br).

The following compounds were prepared from the corresponding mesylates, chlorides or pyridinium-derivatives and secondary amines (In case the reaction was not finished after 20 h, additional amine (5 eq) was added and in cases denoted with * also a catalytic amount of NaI, the reaction was stirred for further 24 h.):

| Example | Compound | MS MH$^+$ | Mp ° C. | Mesylate/Chloride/ pyridinium-derivatives | Secondary amine |
|---------|----------|-----------|---------|-------------------------------------------|-----------------|
| 2.1 | trans-{4-[3-(Allyl-methyl-amino)-prop-1-ynyl]-cyclohexyl}-(5-bromo-pyrimidin-2-yl)-methyl-amine | 377, 1Br | | trans-Methanesulfonic acid 3-{4-[(5-bromo-pyrimidin-2-yl)-methyl-amino]-cyclohexyl}-prop-2-ynyl ester | N-Allylmethyl-amine |

| Example | Compound | MS MH+ | Mp °C. | Mesylate/Chloride/ pyridinium-derivatives | Secondary amine |
|---|---|---|---|---|---|
| 2.2 | trans-(5-Bromo-pyrimidin-2-yl)-methyl-{4-[3-(methyl-propyl-amino)-prop-1-ynyl]-cyclohexyl}-amine | 379, 1Br | | trans-Methanesulfonic acid 3-{4-[(5-bromo-pyrimidin-2-yl)-methyl-amino]-cyclohexyl}-prop-2-ynyl ester | N-Methylpropyl-amine |
| 2.3 | trans-(5-Bromo-pyrimidin-2-yl)-(4-{3-[ethyl-(2-methoxy-ethyl)-amino]-prop-1-ynyl}-cyclohexyl)-methyl-amine | 409, 1Br | | trans-Methanesulfonic acid 3-{4-[(5-bromo-pyrimidin-2-yl)-methyl-amino]-cyclohexyl}-prop-2-ynyl ester | N-(2-Methoxyethyl)-ethyl-amine |
| 2.4 | trans-[2-[(3-{4-[(5-Bromo-pyrimidin-2-yl)-methyl-amino]-cyclohexyl}-prop-2-ynyl)-ethyl-amino]-ethanol] | 395, 1Br | | trans-Methanesulfonic acid 3-{4-[(5-bromo-pyrimidin-2-yl)-methyl-amino]-cyclohexyl}-prop-2-ynyl ester | Ethyl-(2-hydroxy-ethyl)-amine |
| 2.5 | trans-[(5-Bromo-pyrimidin-2-yl)-methyl-[4-(3-piperidin-1-yl-prop-1-ynyl)-cyclohexyl]-amine] | 391, 1Br | | trans-Methanesulfonic acid 3-{4-[(5-bromo-pyrimidin-2-yl)-methyl-amino]-cyclohexyl}-prop-2-ynyl ester | Piperidine |
| 2.6 | trans-[(5-Bromo-pyrimidin-2-yl)-[4-(3-diethylamino-prop-1-ynyl)-cyclohexyl]-methyl-amine] | 379, 1Br | | trans-Methanesulfonic acid 3-{4-[(5-bromo-pyrimidin-2-yl)-methyl-amino]-cyclohexyl}-prop-2-ynyl ester | Diethylamine |
| 2.7 | trans-[4-(3-Dimethylamino-prop-1-ynyl)-cyclohexyl]-methyl-pyrimidin-2-yl-amine | 273 | | trans-Methanesulfonic acid 3-[4-(methyl-pyrimidin-2-yl-amino)-cyclohexyl]-prop-2-ynyl ester | Dimethylamine, 33% in EtOH 5.6 M |
| 2.8 | trans-(6-Chloro-pyridazin-3-yl)-[4-(3-dimethylamino-prop-1-ynyl)-cyclohexyl]-methyl-amine | 307, 1Cl | 90–94, dec. | trans-Methanesulfonic acid 3-{4-[(6-chloro-pyridazin-3-yl)-methyl-amino]-cyclohexyl}-prop-2-ynyl ester | Dimethylamine, 33% in EtOH 5.6 M |
| 2.9 | trans-2-[(3-{4-[(6-Chloro-pyridazin-3-yl)-methyl-amino]-cyclohexyl}-prop-2-ynyl)-ethyl-amino]-ethanol * | 351, 1Cl | | trans-Methanesulfonic acid 3-{4-[(6-chloro-pyridazin-3-yl)-methyl-amino]-cyclohexyl}-prop-2-ynyl ester | Ethyl-(2-hydroxy-ethyl)-amine |
| 2.10 | trans-(6-Chloro-pyridazin-3-yl)-methyl-[4-(3-piperidin-1-yl-prop-1-ynyl)-cyclohexyl]-amine | 347, 1Cl | | trans-Methanesulfonic acid 3-{4-[(6-chloro-pyridazin-3-yl)-methyl-amino]-cyclohexyl}-prop-2-ynyl ester | Piperidine |
| 2.11 | trans-(6-Chloro-pyridazin-3-yl)-methyl-[4-(3-pyrrolidin-1-yl-prop-1-ynyl)-cyclohexyl]-amine | 333, 1Cl | | trans-Methanesulfonic acid 3-{4-[(6-chloro-pyridazin-3-yl)-methyl-amino]-cyclohexyl}-prop-2-ynyl ester | Pyrrolidine |
| 2.12 | trans-(6-Chloro-pyridazin-3-yl)-[4-(3-diethylamino-prop-1-ynyl)-cyclohexyl]-methyl-amine | 335, 1Cl | 51–53, dec. | trans-Methanesulfonic acid 3-{4-[(6-chloro-pyridazin-3-yl)-methyl-amino]-cyclohexyl}-prop-2-ynyl ester | Diethylamine |
| 2.13 | trans-(6-Chloro-pyridazin-3-yl)-methyl-{4-[3-(methyl-propyl-amino)-prop-1-ynyl]-cyclohexyl}-amine | 335, 1Cl | | trans-Methanesulfonic acid 3-{4-[(6-chloro-pyridazin-3-yl)-methyl-amino]-cyclohexyl}-prop-2-ynyl ester | N-Methylpropyl-amine |
| 2.14 | trans-(5-Chloro-pyrimidin-2-yl)-[4-(3-dimethylamino-prop-1-ynyl)-cyclohexyl]-methyl-amine | 307, 1Cl | | trans-Methanesulfonic acid 3-{4-[(5-chloro-pyrimidin-2-yl)-methyl-amino]-cyclohexyl}-prop-2-ynyl ester | Dimethylamine, 33% in EtOH 5.6 M |

-continued

| Example | Compound | MS MH+ | Mp °C. | Mesylate/Chloride/ pyridinium-derivatives | Secondary amine |
|---|---|---|---|---|---|
| 2.15 | trans-2-[(3-{4-[(5-Chloro-pyrimidin-2-yl)-methyl-amino]-cyclohexyl}-prop-2-ynyl)-ethyl-amino]-ethanol | 351, 1Cl | | trans-Methanesulfonic acid 3-{4-[(5-chloro-pyrimidin-2-yl)-methyl-amino]-cyclohexyl}-prop-2-ynyl ester | Ethyl-(2-hydroxy-ethyl)-amine |
| 2.16 | trans-(5-Chloro-pyrimidin-2-yl)-methyl-[4-(3-piperidin-1-yl-prop-1-ynyl)-cyclohexyl]-amine | 347, 1Cl | 58–60° C. dec. | trans-Methanesulfonic acid 3-{4-[(5-chloro-pyrimidin-2-yl)-methyl-amino]-cyclohexyl}-prop-2-ynyl ester | Piperidine |
| 2.17 | trans-(5-Bromo-pyridin-2-yl)-[4-(3-dimethylamino-prop-1-ynyl)-cyclohexyl]-methyl-amine | 350, 1Br | | trans-Methanesulfonic acid 3-{4-[(5-bromo-pyridin-2-yl)-methyl-amino]-cyclohexyl}-prop-2-ynyl ester | Dimethylamine, 33% in EtOH 5.6 M |
| 2.18 | trans-2-[(3-{4-[(5-Bromo-pyridin-2-yl)-methyl-amino]-cyclohexyl}-prop-2-ynyl)-ethyl-amino]-ethanol * | 394, 1 Br | | trans-Methanesulfonic acid 3-{4-[(5-bromo-pyridin-2-yl)-methyl-amino]-cyclohexyl}-prop-2-ynyl ester | Ethyl-(2-hydroxy-ethyl)-amine |
| 2.19 | trans-[4-(3-Dimethylamino-prop-1-ynyl)-cyclohexyl]-methyl-pyridin-2-yl-amine | 272 | | trans-Methanesulfonic acid 3-[4-(methyl-pyridin-2-yl-amino)-cyclohexyl]-prop-2-ynyl ester | Dimethylamine, 33% in EtOH 5.6 M |
| 2.20 | trans-[4-(3-Dimethylamino-prop-1-ynyl)-cyclohexyl]-methyl-pyrazin-2-yl-amine | 273 | 55–57 | trans-Methanesulfonic acid 3-[4-(methyl-pyrazin-2-yl-amino)-cyclohexyl]-prop-2-ynyl ester | Dimethylamine, 33% in EtOH 5.6 M |
| 2.21 | trans-6-(Methyl-{4-[3-(methyl-propyl-amino)-prop-1-ynyl]-cyclohexyl}-amino)-nicotinonitrile | 325 | | trans-Methanesulfonic acid 3-{4-[(5-cyano-pyridin-2-yl)-methyl-amino]-cyclohexyl}-prop-2-ynyl ester | N-Methylpropyl-amine |
| 2.22 | trans-6-{Methyl-[4-(3-piperidin-1-yl-prop-1-ynyl)-cyclohexyl]-amino}-nicotinonitrile | 337 | 114–116 | trans-Methanesulfonic acid 3-{4-[(5-cyano-pyridin-2-yl)-methyl-amino]-cyclohexyl}-prop-2-ynyl ester | Piperidine |
| 2.23 | trans-6-{[4-(3-Dimethylamino-prop-1-ynyl)-cyclohexyl]-methyl-aminol-nicotinonitrile | 297 | | trans-Methanesulfonic acid 3-{4-[(5-cyano-pyridin-2-yl)-methyl-amino]-cyclohexyl}-prop-2-ynyl ester | Dimethylamine, 33% in EtOH 5.6 M |
| 2.24 | trans-(5-Ethyl-pyrimidin-2-yl)-methyl-[4-(3-piperidin-1-yl-prop-1-ynyl)-cyclohexyl]-amine | 341 | | trans-1-(3-{4-[(5-Ethyl-pyrimidin-2-yl)-methyl-amino]-cyclohexyl}-prop-2-ynyl)-pyridinium; methanesulfonate | Piperidine |
| 2.25 | trans-[4-(3-Dimethylamino-prop-1-ynyl)-cyclohexyl]-(5-ethyl-pyrimidin-2-yl)-methyl-amine | 301 | | trans-1-(3-{4-[(5-Ethyl-pyrimidin-2-yl)-methyl-amino]-cyclohexyl}-prop-2-ynyl)-pyridinium; methanesulfonate | Dimethylamine, 33% in EtOH 5.6 M |
| 2.26 | trans-[4-(3-Dimethylamino-prop-1-ynyl)-cyclohexyl]-methyl-(6-methyl-pyridazin-3-yl)-amine | 287 | | trans-[4-(3-Chloro-prop-1-ynyl)-cyclohexyl]-methyl-(6-methyl-pyridazin-3-yl)-amine | Dimethylamine, 33% in EtOH 5.6 M |
| 2.27 | trans-2-[Ethyl-(3-{4-[methyl-(6-methyl-pyridazin-3-yl)-amino]-cyclohexyl}-prop-2-ynyl)-amino]-ethanol | 331 | | trans-[4-(3-Chloro-prop-1-ynyl)-cyclohexyl]-methyl-(6-methyl-pyridazin-3-yl)-amine | Ethyl-(2-hydroxy-ethyl)-amine |

Example 3

3.1
A suspension of 3.4 g (12.72 mmol) of trans-[4-(3-Hydroxy-prop-1-ynyl)-cyclohexyl]-methyl-carbamic acid tert-butyl ester in 125 ml ethanol and 810 mg of $PtO_2 \cdot H_2O$ was hydrogenated (1 atm) for 7 h. The reaction was filtered (Celite) and evaporated to give 3.5 g (quantitative) of trans-[4-(3-Hydroxy-propyl)-cyclohexyl]-methyl-carbamic acid tert-butyl ester, MS: 271 (M).

3.2
In analogy to example 1.6, trans-[4-(3-Hydroxy-propyl)-cyclohexyl]-methyl-carbamic acid tert-butyl gave trans-3-(4-Methylamino-cyclohexyl)-propan-1-ol, MS: 172 ($MH^+$).

3.3
In analogy to example 1.7, trans-3-(4-Methylamino-cyclohexyl)-propan-1-ol gave trans-3-{4-[(5-Bromo-pyrimidin-2-yl)-methyl-amino]-cyclohexyl}-propan-1-ol, MS: 328 ($MH^+$, 1Br).

3.4
In analogy to example 1.17, trans-3-{4-[(5-Bromo-pyrimidin-2-yl)-methyl-amino]-cyclohexyl}-propan-1-ol gave after 5 h trans-Methanesulfonic acid 3-{4-[(5-bromo-pyrimidin-2-yl)-methyl-amino]-cyclohexyl}-propyl ester, MS: 406 ($MH^+$, 1Br).

Example 4

A solution of 209 mg (corresponding to 0.50 mmol) of crude trans-Methanesulfonic acid 3-{4-[(5-bromo-pyrimidin-2-yl)-methyl-amino]-cyclohexyl}-propyl ester in 5 ml of methanol was treated with 0.89 ml (5 mmol) Dimethylamine (33% in EtOH, 5.6M) and stirred over night at RT. After the addition of 0.45 ml (2.5 mmol) Dimethylamine (33% in EtOH, 5.6M), the reaction was stirred for 66 h, then heated at 70° C. for 2 h, cooled, evaporated and the residue extracted with aqueous saturated $NaHCO_3/Et_2O$ (3×). The organic phase was dried with $Na_2SO_4$, filtered and evaporated. Purification by flash column chromatography on silica gel ($CH_2Cl_2$/MeOH 97:3 to 94:6) gave 157 mg (88%) of trans-(5-Bromo-pyrimidin-2-yl)-[4-(3-dimethylamino-propyl)-cyclohexyl]-methyl-amine, MS: 355 ($MH^+$, 1Br).

The following compounds were prepared from the corresponding mesylates and secondary amines. (In case the reaction was not finished, it was heated at reflux until completion of the reaction):

Example 5

5.1
A solution of 10.0 g (25.2 mmol) of trans-[4-(2,2-Dibromo-vinyl)-cyclohexyl]-methyl-carbamic acid tert-butyl ester in 400 ml THF was treated at −78° C. with 33.0 ml (68.3 mmol) of BuLi (ca 1.6 M in hexane) and stirred for 2 h, then 27.8 ml (230.4 mmol) of DMPU were added and 10 min later 19.0 ml (125.9 mmol) of 2-(2-bromoethoxy)tetrahydro-2H-pyran dissolved in 20 ml were dropped in during 20 min. The reaction was warmed up to RT and stirred over night (approx. 16 h). An aqueous solution of saturated $NH_4Cl$ was added and the mixture was extracted with $Et_2O$ (3×). The organic phase was washed with $H_2O$ (2×), aqueous 10% NaCl and dried with $Na_2SO_4$, filtered and evaporated to give after flash column chromatography on silica gel (hexane/EtOAc 19:1 to 3:1) 3.5 g (38%) of trans-Methyl-{4-[4-(tetrahydro-pyran-2-yloxy)-but-1-ynyl]-cyclohexyl}-carbamic acid tert-butyl ester, MS: 366 ($MH^+$).

5.2
A solution of 3.45 g (9.44 mmol) of trans-Methyl-{4-[4-(tetrahydro-pyran-2-yloxy)-but-1-ynyl]-cyclohexyl}-carbamic acid tert-butyl ester and 0.7 g (2.83 mmol) of pyrimidium toluene-4-sulfonate in 25 ml MeOH was stirred at 55° C. for 1.5 h. The reaction was partitioned between aqueous solution of 10% $KHSO_4/Et_2O$ (3×). The organic phases were washed with aqueous saturated $NaHCO_3$, 10% NaCl, dried over $Na_2SO_4$ and evaporated to give 2.85 g (quantitative) of trans-[4-(4-Hydroxy-but-1-ynyl)-cyclohexyl]-methyl-carbamic acid tert-butyl ester, MS: 281 (M).

5.3
In analogy to example 1.6, trans-[4-(4-Hydroxy-but-1-ynyl)-cyclohexyl]-methyl-carbamic acid tert-butyl ester with TFA was converted to trans-4-(4-Methylamino-cyclohexyl)-but-3-yn-1-ol, MS: 182 ($MH^+$).

5.4
A mixture of 1.06 g (5.85 mmol) trans-4-(4-Methylamino-cyclohexyl)-but-3-yn-1-ol, 1.67 g (7.02 mmol) of 2,5-dibromo-pyrimidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] and 3.38 ml (19.88 mmol) N-ethyldiisopropylamine were heated for 2 h

| Example | Compound | MS $MH^+$ | Mesylate | Secondary amine |
| --- | --- | --- | --- | --- |
| 4.1 | trans-{4-[3-(Allyl-methyl-amino)-propyl]-cyclohexyl}-(5-bromo-pyrimidin-2-yl)-methyl-amine | 381, 1Br | trans-Methanesulfonic acid 3-{4-[(5-bromo-pyrimidin-2-yl)-methyl-amino]-cyclohexyl}-propyl ester | N-Allylmethyl-amine |
| 4.2 | trans-(5-Bromo-pyrimidin-2-yl)-methyl-{4-[3-(methyl-propyl-amino)-propyl]-cyclohexyl}-amine | 383, 1Br | trans-Methanesulfonic acid 3-{4-[(5-bromo-pyrimidin-2-yl)-methyl-amino]-cyclohexyl}-propyl ester | N-Methylpropyl-amine |
| 4.3 | trans-(5-Bromo-pyrimidin-2-yl)-(4-{3-[ethyl-(2-methoxy-ethyl)-amino]-propyl}-cyclohexyl)-methyl-amine | 413, 1Br | trans-Methanesulfonic acid 3-{4-[(5-bromo-pyrimidin-2-yl)-methyl-amino]-cyclohexyl}-propyl ester | N-(2-Methoxyethyl)ethylamine | at 85° C., diluted with 1 ml DMA and heated for 3.5 h at 85° C. The reaction was cooled, evaporated and partitioned between aqueous saturated NaHCO$_3$/Et$_2$O (3×). The organic phases were washed with aqueous 10% NaCl, dried (NaSO$_4$) and evaporated. Flash chromatography on silica gel (hexane/EtOAc 9:1 to 1:1) gave 1.37 g (69%) of trans-4-{4-[(5-Bromo-pyrimidin-2-yl)-methyl-amino]-cyclohexyl}-but-3-yn-1-ol, MS: 338 (MH$^+$, 1Br).

5.5

In analogy to example 1.17, trans-4-{4-[(5-Bromo-pyrimidin-2-yl)-methyl-amino]-cyclohexyl}-but-3-yn-1-ol was converted to trans-Methanesulfonic acid 4-{4-[(5-bromo-pyrimidin-2-yl)-methyl-amino]-cyclohexyl}-but-3-ynyl ester, MS: 416 (MH$^+$, 1Br).

Example 6

6.1

A solution of 211 mg (0.51 mmol) of crude trans-Methanesulfonic acid 4-{4-[(5-bromo-pyrimidin-2-yl)-methyl-amino]-cyclohexyl}-but-3-ynyl ester in 5 ml of methanol was treated with 0.91 ml (5.1 mmol) Dimethylamine (33% in EtOH, 5.6M) and heated at 65° C. for 4 h. After cooling and evaporation, the residue was extracted with aqueous saturated NaHCO$_3$/Et$_2$O (3×). The organic phase was dried (Na$_2$SO$_4$), filtered and evaporated. Purification by flash column chromatography on silica gel (CH$_2$Cl$_2$/MeOH 99:1 to 95:5) gave 141 mg (76%) of trans-(5-Bromo-pyrimidin-2-yl)-[4-(4-dimethylamino-but-1-ynyl)-cyclohexyl]-methyl-amine, MS: 365 (MH$^+$, 1Br).

6.2

In analogy to example 6.1, trans-Methanesulfonic acid 4-{4-[(5-bromo-pyrimidin-2-yl)-methyl-amino]-cyclohexyl}-but-3-ynyl ester and piperidine gave after 4.5 h at 65° C., trans-(5-Bromo-pyrimidin-2-yl)-methyl-[4-(4-piperidin-1-yl-but-1-ynyl)-cyclohexyl]-amine, MS: 405 (MH$^+$, 1Br).

Example 7

7.1

In analogy to example 3.1, trans-[4-(4-Hydroxy-but-1-ynyl)-cyclohexyl]-methyl-carbamic acid tert-butyl ester was converted to trans-[4-(4-Hydroxy-butyl)-cyclohexyl]-methyl-carbamic acid tert-butyl ester, MS: 286 (MH$^+$).

7.2

In analogy to example 1.6, trans-[4-(4-Hydroxy-butyl)-cyclohexyl]-methyl-carbamic acid tert-butyl ester was converted to trans-4-(4-Methylamino-cyclohexyl)-butan-1-ol, MS: 186 (MH$^+$).

7.3

In analogy to example 1.7, trans-4-(4-Methylamino-cyclohexyl)-butan-1-ol and 2,5-dibromo-pyrimidine was converted to trans-4-{4-[(5-Bromo-pyrimidin-2-yl)-methyl-amino]-cyclohexyl}-butan-1-ol, MS: 342 (MH$^+$, 1Br).

7.4

In analogy to example 1.17, trans-4-{4-[(5-Bromo-pyrimidin-2-yl)-methyl-amino]-cyclohexyl}-butan-1-ol yielded after 2.5 h trans-Methanesulfonic acid 4-{4-[(5-bromo-pyrimidin-2-yl)-methyl-amino]-cyclohexyl}-butyl ester, MS: 420 (MH$^+$, 1Br).

Example 8

8.1

In analogy to example 6.1, trans-Methanesulfonic acid 4-{4-[(5-bromo-pyrimidin-2-yl)-methyl-amino]-cyclohexyl}-butyl ester and Dimethylamine (33% in EtOH, 5.6M) gave after 4 h at 65° C., trans-(5-Bromo-pyrimidin-2-yl)-[4-(4-dimethylamino-butyl)-cyclohexyl]-methyl-amine, MS: 369 (MH$^+$, 1Br).

8.2

In analogy to example 6.1, trans-Methanesulfonic acid 4-{4-[(5-bromo-pyrimidin-2-yl)-methyl-amino]-cyclohexyl}-butyl ester and piperidine gave after 7 h at 65° C., trans-(5-Bromo-pyrimidin-2-yl)-methyl-[4-(4-piperidin-1-yl-butyl)-cyclohexyl]-amine, MS: 409 (MH$^+$, 1Br).

Example 9

9.1

A well stirred solution of 100 g (774 mmol) of cis-4-Methylamino-cyclohexanol [Schut, Robert N. Analgesic 3-(methylamino)-1,2,3,4-tetrahydrocarbazole from 4-(methylamino)cyclohexanone. Fr. (1968), 3 pp. FR 1515629 19680301] in 775 ml EtOAc was treated with 1.55 l of aqueous 1M NaHCO$_3$ and with 110 ml (774 mmol) of benzyl chloroformate (30 min, Tmax 30° C.). The phases were separated after 2 h at RT. The aqueous phase was extracted (EtOAc), the organic phases were dried (Na$_2$SO$_4$), filtered and evaporated. Purification by column chromatography on silica gel (hexane/EtOAc 2:1) gave 139 g (68%) of cis-(4-Hydroxy-cyclohexyl)-methyl-carbamic acid benzyl ester, MS: 263 (M).

9.2

A solution of 2.63 g (10 mmol) of cis-(4-Hydroxy-cyclohexyl)-methyl-carbamic acid benzyl ester in 16 ml CH$_2$Cl$_2$ was treated with a solution 0.24 g (2 mmol) of KBr and 0.28 g (3.33 mmol) of NaHCO$_3$ in 5 ml of water. The suspension was cooled (0–5° C.) and 8 mg (0.05 mmol) of TEMPO and then 5.7 ml (12.5 mmol) of NaOCl (13%, 2.18 M in water) were added during 20 min. After 1 h at this temperature, again 8 mg (0.05 mmol) of TEMPO and then 2.85 ml (6.25 mmol) of NaOCl (13%, 2.18 M in water) were added. After 1 h, 5 ml of 1M sodium thiosulfat solution was added. The aqueous phase was extracted with CH$_2$Cl$_2$(2×), the organic phase was dried (Na$_2$SO$_4$), filtered and evaporated to give 2.57 g (99%) of Methyl-(4-oxo-cyclohexyl)-carbamic acid benzyl ester, MS: 261 (M).

9.3

A suspension of 749.88 g (2187.5 mmol) (methoxymethyl)triphenylphosphonium chloride in 2.5 l THF was cooled (–10° C.) and deprotonated with 245.5 g (2187.5 mmol) potassium t-butoxide. The dark red solution was stirred at 0–5° C. for 0.5 h, cooled (–20° C.) and 457.32 g (261.33 mmol) of Methyl-(4-oxo-cyclohexyl)-carbamic acid benzyl ester in 1.25 l THF were dropped in (1.25 h). After 1.3 h at RT, the reaction was treated with 1.75 l aqueous 1M NaHCO$_3$ and stirred for 45 min. The phases were separated, the aqueous phase was extracted with TBME (700 ml), the organic phase was dried (Na$_2$SO$_4$), filtered and evaporated. The residue was suspended in hexane (5 l), cooled (0° C.), filtered and evaporated to give 495.2 g (98%) of (4-Methoxymethylene-cyclohexyl)-methyl-carbamic acid benzyl ester, MS: 289 (M).

9.4

A solution of 495 g (1710.6 mmol) of (4-Methoxymethylene-cyclohexyl)-methyl-carbamic acid benzyl ester in 1.7 l THF was treated at RT with 3.42 l of aqueous 1N HCl and heated at reflux for 2 h. The reaction was cooled to RT and extracted with TBME (1.7 and 0.9 l). The organic phase was washed with aqueous 1M NaHCO$_3$, dried (Na$_2$SO$_4$), filtered and evaporated to give 457.4 (97%) of crude (4-Formyl-cyclohexyl)-methyl-carbamic acid benzyl ester (trans:cis ca 70:30).

A solution of 327 g (1188 mmol) of crude (4-Formyl-cyclohexyl)-methyl-carbamic acid benzyl ester in 1.64 l TBME was added at RT to a solution of 451.5 g (2375 mmol) of disodium pyrosulfite in 1.64 l water. The reaction was stirred for 15 h, filtered and washed (1.1 l TBME) to give 191.7 g (45%) of the sodium salt of [4-(Benzyloxycarbonyl-methyl-amino)-cyclohexyl]-hydroxy-methane-sulfonic acid (trans:cis 95:5). This compound was suspended in 0.5 l TBME and 1.01 l aqueous 1M Na$_2$CO$_3$ and stirred for 1 h at RT. The phases were separated, the aqueous phase was extracted with TBME (1 l), the organic phase was dried (Na$_2$SO$_4$), filtered and evaporated to give 128 g (36% over the two steps) of trans-(4-Formyl-cyclohexyl)-methyl-carbamic acid benzyl ester (trans:cis 99:1), MS: 275 (M).

9.5

A suspension of 128.6 g (375 mmol) of (methoxymethyl)triphenylphosphonium chloride in 540 ml THF was treated at −8° C. with 43.1 g (375 mmol) potassium tert-butoxide. The red solution was stirred 30 min at 0° C. and cooled (−20° C.), then 82.6 g (300 mmol) of trans-(4-Formyl-cyclohexyl)-methyl-carbamic acid benzyl ester in 240 ml THF were dropped in (60 min). The reaction was warmed to RT and stirred for 2 h, washed with aqueous saturated NaHCO$_3$ (540 ml). The water phase was extracted with 0.5 l TBME, the combined organic phases were oxidized with 16 ml of hydrogen peroxide solution (35%), mixed with water (150 ml). The organic solvent was evaporated, the residue was extracted with MeOH (350 ml)/hexane (2×2000 ml). The hexane was washed twice with 500 ml MeOH/water (7/3), dried (Na$_2$SO$_4$) and evaporated to give 81.7 g (90%) of trans-(2E/Z) [4-(2-Methoxy-vinyl)-cyclohexyl]-methyl-carbamic acid benzyl ester, MS: 303(M).

9.6

In analogy to example 9.4, trans-(2E/Z) [4-(2-Methoxy-vinyl)-cyclohexyl]-methyl-carbamic acid benzyl ester gave after 1 h reflux, trans-Methyl-[4-(2-oxo-ethyl)-cyclohexyl]-carbamic acid benzyl ester, MS: 290 (MH$^+$).

9.7

A suspension of 77.4 g (267.4 mmol) of trans-Methyl-[4-(2-oxo-ethyl)-cyclohexyl]-carbamic acid benzyl ester, 63.86 g (292.6 mmol) of di-tert-butyl dicarbonate and 7.7 g of Pd/C 10% in 775 ml EtOAc was hydrogenated (1 atm) at 38° C. for 48 h (during the day, every hour, the hydrogen was exchanged). The reaction was filtered (Celite) and evaporated to give after flash silica gel column (hexane/EtOAc 4:1) 38.4 g (56%) of trans-Methyl-[4-(2-oxo-ethyl)-cyclohexyl]-carbamic acid tert-butyl ester, MS: 255 (M).

9.8

In analogy to example 1.4, trans-Methyl-[4-(2-oxo-ethyl)-cyclohexyl]-carbamic acid tert-butyl ester was converted to trans-[4-(3,3-Dibromo-allyl)-cyclohexyl]-methyl-carbamic acid tert-butyl ester, MS: 352 (M-Butene, 2Br).

9.9

In analogy to example 1.5, trans-[4-(3,3-Dibromo-allyl)-cyclohexyl]-methyl-carbamic acid tert-butyl ester was converted to trans-[4-(4-Hydroxy-but-2-ynyl)-cyclohexyl]-methyl-carbamic acid tert-butyl ester, MS: 281 (M).

9.10

In analogy to example 1.6, trans-[4-(4-Hydroxy-but-2-ynyl)-cyclohexyl]-methyl-carbamic acid tert-butyl ester was converted to trans-4-(4-Methylamino-cyclohexyl)-but-2-yn-1-ol, MS: 182 (MH$^+$).

9.11

In analogy to example 1.15, trans-4-(4-Methylamino-cyclohexyl)-but-2-yn-1-ol and 3,6-dichloropyridazine gave, with no NaI after 6 h at 80° C. and ¾h at 120° C. in the microwave oven, trans-4-{4-[(6-Chloro-pyridazin-3-yl)-methyl-amino]-cyclohexyl}-but-2-yn-1-ol, MS: 294 (MH$^+$, 1Cl).

9.12

In analogy to example 1.15, trans-4-(4-Methylamino-cyclohexyl)-but-2-yn-1-ol and 1.2 eq of 2,5-dibromo-pyrimidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] gave, with no NaI after 6 h at 80° C. and ¼ h at 120° C. in the microwave oven, trans-4-{4-[(5-Bromo-pyrimidin-2-yl)-methyl-amino]-cyclohexyl}-but-2-yn-1-ol, MS: 338 (MH$^+$, 1Br).

9.13

A solution of 1.08 g (3.68 mmol) of trans-4-{4-[(6-Chloro-pyridazin-3-yl)-methyl-amino]-cyclohexyl}-but-2-yn-1-ol in 30 ml CH$_2$Cl$_2$ was treated at 0° C. with 0.31 ml (4.04 mmol) methanesulfonylchloride and 0.64 ml (5.51 mmol) 2,6-lutidine. The reaction was stirred for 46 h at room temperature, water (4 ml) was added and stirred for 5 min. After extraction with aqueous saturated NaHCO$_3$/Et$_2$O(3×), the organic phase was washed with aqueous 10% NaCl, dried over Na$_2$SO$_4$ and evaporated to yield 1.45 g of crude trans-Methanesulfonic acid 4-{4-[(6-chloro-pyridazin-3-yl)-methyl-amino]-cyclohexyl}-but-2-ynyl ester, MS: 372 (MH$^+$, 1Cl).

9.14

In analogy to example 9.13, trans-4-{4-[(5-Bromo-pyrimidin-2-yl)-methyl-amino]-cyclohexyl}-but-2-yn-1-ol was converted to trans-methanesulfonic acid 4-{4-[(5-bromo-pyrimidin-2-yl)-methyl-amino]-cyclohexyl}-but-2-ynyl ester, MS: 416 (MH$^+$, 1Br).

Example 10

In analogy to example 2, the following compounds were prepared from the corresponding mesylates and secondary amines:

| Example | Compound | MS MH$^+$ | Mesylate | Secondary amine |
| --- | --- | --- | --- | --- |
| 10.1 | trans-(6-Chloro-pyridazin-3-yl)-[4-(4-dimethylamino-but-2-ynyl)-cyclohexyl]-methyl-amine | 321, 1Cl | trans-Methanesulfonic acid 4-{4-[(6-chloro-pyridazin-3-yl)-methyl-amino]-cyclohexyl}-but-2-ynyl ester | Dimethylamine, 33% in EtOH 5.6 M |

| Example | Compound | MS MH+ | Mesylate | Secondary amine |
|---|---|---|---|---|
| 10.2 | trans-(6-Chloro-pyridazin-3-yl)-methyl-[4-(4-piperidin-1-yl-but-2-ynyl)-cyclohexyl]-amine | 361, 1Cl | trans-Methanesulfonic acid 4-{4-[(6-chloro-pyridazin-3-yl)-methyl-amino]-cyclohexyl}-but-2-ynyl ester | Piperidine |
| 10.3 | trans-(5-Bromo-pyrimidin-2-yl)-[4-(4-dimethylamino-but-2-ynyl)-cyclohexyl]-methyl-amine | 365, 1Br | trans-methanesulfonic acid 4-{4-[(5-bromo-pyrimidin-2-yl)-methyl-amino]-cyclohexyl}-but-2-ynyl ester | Dimethylamine, 33% in EtOH 5.6 M |
| 10.4 | trans-(5-Bromo-pyrimidin-2-yl)-methyl-[4-(4-piperidin-1-yl-but-2-ynyl)-cyclohexyl]-amine | 395, 1Br | trans-methanesulfonic acid 4-{4-[(5-bromo-pyrimidin-2-yl)-methyl-amino]-cyclohexyl}-but-2-ynyl ester | Piperidine |

Example 11

11.1

To a dry-ice cooled solution of 30.0 g (208 mmol) of trans-(4-hydroxymethyl-cyclohexyl)-methanol in 450 ml tetrahydrofuran was dropped at −60° C. to −67° C., within 30 minutes, 130 ml (208 mmol) of 1.6 M butyllithium solution (1.6 M in hexane). After stirring for 30 minutes at −78° C., 32.3 g (208 mmol) of tert-butyl-dimethyl-chlorosilane was added within 10 minutes. After 15 minutes at −65° C., the reraction was stirred over night at room temperature and then partitioned between Et2O, 1N hydrogen chloride solution and water. The organic layer was dried over magnesium sulfate, concentrated under reduced pressure and the residue then chromatographed on silica gel with a 3:1 v/v mixture of hexane and ethylacetate as the eluent giving 27.7 g (51%) of pure trans-[4-(tert-butyl-dimethyl-silanyloxymethyl)-cyclohexyl]-methanol as colorless viscous oil, MS: 259 (MH+).

11.2

To an ice-cooled solution of 27.6 g (107 mmol) of trans-[4-(tert-butyl-dimethyl-silanyloxymethyl)-cyclohexyl]-methanol and 9.99 ml (128 mmol) of methanesulfonyl chloride in 350 ml of dichloromethane was added under stirring at 0–10° C. 29.6 ml (213 mmol) of triethylamine within 20 minutes. The reaction-mixture was stirred for 1 hour at room temperature. It was then partitioned between dichloromethane, 1N HCl and water. The dichloromethane-phase was dried over magnesium sulfate and concentrated to yield 38.2 g crude trans-methanesulfonic acid 4-(tert-butyl-dimethyl-silanyloxymethyl)-cyclohexylmethyl ester as colorless viscous oil, MS: 354 (M+NH4+).

11.3

38.2 g of crude trans-methanesulfonic acid 4-(tert-butyl-dimethyl-silanyloxymethyl)-cyclohexylmethyl ester and 16.7 g (340 mmol) of sodium cyanide dissolved in 380 ml of N,N-dimethylformamide were stirred for 2 hours at 80° C. After cooling the reaction mixture down to room temperature, it was partitioned between Et2O and water. The organic layer was dried over magnesium sulfate and concentrated under reduced pressure and the residue then chromatographed on silica gel with a 9:1 v/v mixture of hexane and ethylacetate as the eluent giving 24.2 g (78% over two steps) of pure trans-[4-(tert-butyl-dimethyl-silanyloxymethyl)-cyclohexyl]-acetonitrile as colorless viscous oil, MS: 290 (MNa+).

11.4

A solution of 24.2 g (90.5 mmol) of trans-[4-(tert-butyl-dimethyl-silanyloxymethyl)-cyclohexyl]-acetonitrile, of 22 ml (270 mmol) chloroform and of 2.4 g $PtO_2.H_2O$ (Degussa 223) in 250 ml ethanol was stirred at room temperature for 20 hours under a hydrogen atmosphere. The catalyst was then removed by filtration and the solvent evaporated under reduced pressure giving. 17.1 g (97%) of pure trans-[4-(2-amino-ethyl)-cyclohexyl]-methanol HCl-salt as colorless solid, MS: 158 (MH+).

11.5

In analogy to example 5.4, trans-[4-(2-amino-ethyl)-cyclohexyl]-methanol HCl-salt with 5.4 eq N-ethyldiisopropylamine and 1.2 eq 2,5-dibromo-pyrimidine in DMA for 7.5 h at 85° C. gave trans-{4-[2-(5-Bromo-pyrimidin-2-ylamino)-ethyl]-cyclohexyl}-methanol, mp: 151.7–153.4° C.; MS: 314 (MH+, 1Br).

11.6

A solution of 481 mg (1.53 mmol) of trans-{4-[2-(5-Bromo-pyrimidin-2-ylamino)-ethyl]-cyclohexyl}-methanol in 14 ml $CH_2Cl_2$ was treated at 0 C with 0.13 ml (1.68 mmol) methanesulfonylchloride and 0.27 ml (2.30 mmol) 2,6-lutidine. The reaction was stirred for 20 h at room temperature, water (2 ml) was added and stirred for 5 min. After extraction with aqueous saturated $NaHCO_3/Et_2O$ (3×), the organic phase was washed with aqueous 10% NaCl, dried over $Na_2SO_4$ and evaporated to yield 970 mg of crude trans-Methanesulfonic acid 4-[2-(5-bromo-pyrimidin-2-ylamino)-ethyl]-cyclohexylmethyl ester, MS: 392 (MH+, 1Br).

11.7

To a solution of 17.6 g (90.9 mmol) trans-[4-(2-amino-ethyl)-cyclohexyl]-methanol HCl-salt and 13.9 ml (100 mmol) triethylamine in 120 ml dichloromethane was added under stirring within 10 minutes at room temperature a solution of 21.8 g (100 mmol) of di-tert-butyl-dicarbonate in 70 ml of dichloromethane. After stirring for 3 hours at room temperature, the reaction-mixture was partitioned between dichloromethane, 1N hydrogen chloride solution and water. Then, the dichloromethane-phase was dried over magnesium sulfate and concentrated to yield 27.9 g of crude trans-[2-(4-hydroxymethyl-cyclohexyl)-ethyl]-carbamic acid tert-butyl ester as colorless viscous oil, MS: 275 (MNH$_4^+$).

11.8

A solution of 27.9 g (86.7 mmol) trans-[2-(4-hydroxymethyl-cyclohexyl)-ethyl]-carbamic acid tert-butyl ester, 41 ml (434 mmol) acetic anhydride and 35 ml (434 mmol) of pyridine in 140 ml of dichloromethane was stirred at room temperature for 16 hours. The reaction-mixture was then taken up in Et$_2$O and washed with 1N hydrogen chloride solution, sodium hydrogen carbonate solution and water. Then, the Et$_2$O-phase was dried over magnesium sulfate and concentrated to yield 26.0 g crude trans-acetic acid 4-(2-tert-butoxycarbonylamino-ethyl)-cyclohexylmethyl ester as colorless viscous oil, MS: 200 [(M-(tert-butoxycarbonyl)) H$^+$].

11.9

To an ice-cooled and stirred solution of the crude 26.0 g trans-acetic acid 4-(2-tert-butoxycarbonylamino-ethyl)-cyclohexylmethyl ester and 5.77 ml (92.6 mmol) methyliodide in 300 ml of N,N-dimethylformamide was added within 15 minutes 4.04 g (92.58 mmol) sodium hydride (55% in oil). After stirring over night at room temperature, additional 1.65 ml (26.5 mmol) methyliodide and 1.16 g (26.5 mmol) of sodium hydride were added and the reaction-mixture was then stirred for another 1 hour at room temperature. It was then partitioned between Et$_2$O, 1N hydrogen chloride solution and water. The organic layer was dried over magnesium sulfate and concentrated under reduced pressure and the residue then chromatographed on silica gel with a 4:1 v/v mixture of hexane and ethylacetate as the eluent giving 18.7 g (68% over 3 steps) of pure trans-acetic acid 4-[2-(tert-butoxycarbonyl-methyl-amino)-ethyl]-cyclohexylmethyl ester as colorless viscous oil, MS: 214 [(M-(tert-butoxycarbonyl)) H$^+$].

11.10

To a solution of 18.7 g (59.7 mmol) of trans-acetic acid 4-[2-(tert-butoxycarbonyl-methyl-amino)-ethyl]-cyclohexylmethyl ester in 110 ml of methanol was added 41.25 g (298.5 mmol) of potassium carbonate. The reaction mixture was then stirred for 2 hours at room temperature. The excess of potassium carbonate was removed by filtration and the methanol was removed by evaporation under reduced pressure. The crude residue was partitioned between Et$_2$O, 1N hydrogen chloride solution and water. The organic layer was dried over magnesium sulfate and concentrated under reduced pressure and the residue then chromatographed on silica gel with a 2:1 v/v mixture of hexane and ethylacetate as the eluent giving 13.9 g (86%) of pure trans-[2-(4-hydroxymethyl-cyclohexyl)-ethyl]-methyl-carbamic acid tert-butyl ester as colorless viscous oil, MS: 272 (MH$^+$).

11.11

A solution of 1.45 g (5.34 mmol) of trans-[2-(4-hydroxymethyl-cyclohexyl)-ethyl]-methyl-carbamic acid tert-butyl ester in 10 ml dioxane was treated at 10° C. with 13.4 ml (53.4 mmol) of HCl in dioxane (4M). After 3.5 h at RT, the reaction was evaporated to give 1.6 g (quantitative) of trans-[4-(2-Methylamino-ethyl)-cyclohexyl]-methanol hydrochloride, MS: 172 (MH$^+$).

11.12

In analogy to example 5.4, trans-[4-(2-Methylamino-ethyl)-cyclohexyl]-methanol hydrochloride with 5.4 eq of N-ethyldiisopropylamine and 1.2 eq of 2,5-dibromo-pyrimidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] was converted (½ h at 85° C. with no solvent and 6 h at 85° C. in DMA) to trans-(4-{2-[(5-Bromo-pyrimidin-2-yl)-methyl-amino]-ethyl}-cyclohexyl)-methanol, mp: 61–63° C.; MS: 328 (MH$^+$, 1Br).

11.13

In analogy to example 11.6, trans-(4-{2-[(5-Bromo-pyrimidin-2-yl)-methyl-amino]-ethyl}-cyclohexyl)-methanol gave trans-Methanesulfonic acid 4-{2-[(5-bromo-pyrimidin-2-yl)-methyl-amino]-ethyl}-cyclohexylmethyl ester, MS: 406 (MH$^+$, 1Br).

Example 12

A solution of 258 mg (corresponding to 0.41 mmol) of crude trans-Methanesulfonic acid 4-[2-(5-bromo-pyrimidin-2-ylamino)-ethyl]-cyclohexylmethyl ester in 5 ml of methanol was treated with 0.73 ml (4.1 mmol) Dimethylamine (33% in EtOH, 5.6M) and heated at 65° C. for 4 h, a catalytic amount of NaI was added and heated for 16 h. After cooling and evaporation, the residue was extracted with aqueous saturated NaHCO$_3$/Et$_2$O (3×). The organic phase was dried (Na$_2$SO$_4$), filtered and evaporated. Purification by flash column chromatography on silica gel (CH$_2$Cl$_2$/MeOH 99:1 to 9:1) gave 105 mg (76%) of trans-(5-Bromo-pyrimidin-2-yl)-[2-(4-dimethylaminomethyl-cyclohexyl)-ethyl]-amine, mp: 108.3–109.5° C.; MS: 341 (MH$^+$, 1Br).

The following compounds were prepared from the corresponding mesylates and secondary amines:

| Example | Compound | MS MH$^+$ | Mp ° C. | Mesylate | Secondary amine |
|---|---|---|---|---|---|
| 12.1 | trans-(5-Bromo-pyrimidin-2-yl)-[2-(4-piperidin-1-ylmethyl-cyclohexyl)-ethyl]-amine | 381, 1Br | 138–139 | trans-Methanesulfonic acid 4-[2-(5-bromo-pyrimidin-2-ylamino)-ethyl]-cyclohexylmethyl ester | Piperidine |
| 12.2 | trans-(5-Bromo-pyrimidin-2-yl)-[2-(4-dimethylaminomethyl-cyclohexyl)-ethyl]-methyl-amine | 355, 1Br | 66–67 | trans-Methanesulfonic acid 4-{2-[(5-bromo-pyrimidin-2-yl)-methyl-amino]-ethyl}-cyclohexylmethyl ester | Dimethylamine, 33% in EtOH 5.6 M |
| 12.3 | trans-(5-Bromo-pyrimidin-2-yl)-methyl-[2-(4-piperidin-1-ylmethyl-cyclohexyl)-ethyl]-amine | 395, 1Br | 76–82 dec. | trans-Methanesulfonic acid 4-{2-[(5-bromo-pyrimidin-2-yl)-methyl-amino]-ethyl}-cyclohexylmethyl ester | Piperidine |

Example 13

13.1

In this reaction, the solvents were degased with argon for 10 minutes. A suspension of 7.3 mg $PdCl_2(dppf)$, of 29.4 mg (0.24 mmol) of 4-pyridylboronic acid an of 70 mg (0.2 mmol) of trans-(5-Bromo-pyrimidin-2-yl)-[4-(3-dimethylamino-prop-1-ynyl)-cyclohexyl]-methyl-amine in 3.5 ml dioxane were treated with 1 ml of an aqueous solution of 2M $Na_2CO_3$. After 17 h at 85° C., 7 mg of $PdCl_2(dppf)$ were added and the reaction was heated further at 85° C. for 24 h. The mixture was partitioned between aqueous saturated $NaHCO_3/Et_2O$ (3×) and the combined organic phases were extracted with 0.1M HCl. The HCl-phase was adjusted to pH 14 (1 N NaOH) and extracted with $Et_2O$ (3×). The organic phase was washed with 10% NaCl and dried over $Na_2SO_4$ to yield after purifiction with flash-chromatography on silica gel ($CH_2Cl_2$/MeOH 99:1 to 9:1) 9 mg (13%) of trans-[4-(3-Dimethylamino-prop-1-ynyl)-cyclohexyl]-methyl-(5-pyridin-4-yl-pyrimidin-2-yl)-amine, MS: 350 ($MH^+$).

13.2

In analogy to example 13.1, trans-(5-Bromo-pyrimidin-2-yl)-[4-(3-dimethylamino-prop-1-ynyl)-cyclohexyl]-methyl-amine and thiophene-3-boronic acid was converted to trans-[4-(3-Dimethylamino-prop-1-ynyl)-cyclohexyl]-methyl-(5-thiophen-3-yl-pyrimidin-2-yl)-amine, MS: 355 ($MH^+$).

Example 14

A solution of 92.1 mg (0.3 mmol) of trans-(6-Chloro-pyridazin-3-yl)-[4-(3-dimethylamino-prop-1-ynyl)-cyclohexyl]-methyl-amine in 0.6 ml DMA was treated with 0.56 ml (3 mmol) of sodium methylate (5.4 M in MeOH) and heated at 80° C. for 54 h. The reaction was extracted with aqueous saturated $NaHCO_3/Et_2O$ (3×). The organic phase was dried ($Na_2SO_4$), filtered and evaporated. Purification by flash column chromatography on silica gel ($CH_2Cl_2$/MeOH 99:1 to 97:3) yielded 67 mg (74%) of pure trans-[4-(3-Dimethylamino-prop-1-ynyl)-cyclohexyl]-(6-methoxy-pyridazin-3-yl)-methyl-amine, MS: 303 ($MH^+$).

Example 15

15.1

A solution of 81 g (314.77 mmol) trans-4-[(tert-Butoxyformamido)methyl]cyclohexanecarboxylic acid in 4 l $CH_2Cl_2$ was treated with 50.13 g (503.63 mmol) N,O-dimethyl-hydroxylamine hydrochloride, 55.37 ml (503.63 mmol) N-methylmorpholine and at 0° C. with 78.45 g (409.2 mmol) EDCI and 9.67 g (62.95 mmol) HOBT. The reaction mixture was stirred 16 h at room temperature, evaporated and extracted with aqueous 10% $KHSO_4/Et_2O$ (3×). The organic phases were washed with aqueous saturated $NaHCO_3$, 10% NaCl and dried over $Na_2SO_4$ to yield 100.03 g (quantitative) of trans-[4-(Methoxy-methyl-carbamoyl)-cyclohexylmethyl]-carbamic acid tert-butyl ester, MS: 301 ($MH^+$).

15.2

A solution of 95 g (corresponds to 301.26 mmol) of crude trans-[4-(Methoxy-methyl-carbamoyl)-cyclohexylmethyl]-carbamic acid tert-butyl ester in 300 ml of DMA was treated at 0° C. with 19.72 g (451.9 mmol) of NaH (55% in oil) in small portions. The reaction was stirred for 1 h at 0° C., then treated slowly (1.5 h) with 150 ml (2.41 mol) of iodomethane. After the addition of 60 ml of iodomethane (1 h), the reaction started, the addition was stopped and continued after reaction was cooled down again. After warming up to RT over night, the reaction was cooled, neutralized with aqueous 10% $KHSO_4$ and poured into water/$Et_2O$ (3×). The organic phase was washed with aqueous 10% NaCl, dried over $Na_2SO_4$ evaporated and purified by flash silica gel column ($CH_2Cl_2$/EtOAc 9:1 to 1:1) to yield 99 g (quantitative) of trans-[4-(Methoxy-methyl-carbamoyl)-cyclohexylmethyl]-methyl-carbamic acid tert-butyl ester, MS: 315 ($MH^+$).

15.3

A solution of 12.25 g (313.11 mmol) LAH in 1.3 l THF was cooled (−50° C.) and treated during 30 min with a solution of 89.5 g (284.64 mmol) of trans-[4-(Methoxy-methyl-carbamoyl)-cyclohexylmethyl]-methyl-carbamic acid tert-butyl ester in 1.3 l THF. After 20 min at this temperature, the reaction was warmed up to 0° C., cooled (−78° C.) and hydrolyzed with a suspension of 90 g $MgSO_4 \cdot 7H_2O$, 90 g silicagel in 292 ml aqueous 10% $KHSO_4$. The cooling bath was removed, THF was added, the mixture was stirred for 30 min and filtered. After evaporation, the residue was dissolved in $CH_2Cl_2$, dried over $Na_2SO_4$ and evaporated to yield 90.4 (quantitative) of trans-(4-Formyl-cyclohexylmethyl)-methyl-carbamic acid tert-butyl ester, MS: 255 (M).

15.4

A solution of 257.6 g (982 mmol) triphenylphosphine in 1 l $CH_2Cl_2$ was treated with 162.8 g (491 mmol) tetrabromomethane (the reaction heated up to reflux and was then cooled with an ice bath) and after 40 min at RT with 157.4 ml (1129 mmol) triethylamine (the reaction heated up to reflux and became dark violet). After cooling (0° C.), 77.96 g (corresponds to 245.5 mmol) of crude trans-(4-Formyl-cyclohexylmethyl)-methyl-carbamic acid tert-butyl ester in 600 ml $CH_2Cl_2$ were added during 20 min. The solution was stirred for 20 h at RT, evaporated and filtered through silica gel (deactivated with hexane/0.5% Et3N) with hexane/$Et_2O$ 99:1 to 4:1 as eluent to yield 61.5 g (61%) of trans-[4-(2,2-Dibromo-vinyl)-cyclohexylmethyl]-methyl-carbamic acid tert-butyl ester, MS: 409 (M, 2Br).

15.5

The following reaction was performed in analogy to the reaction described in: Marshall, James A.; Bartley, Gary S.; Wallace, Eli M. Total Synthesis of the Pseudopterane (−)-Kallolide B, the Enantiomer of Natural (+)-Kallolide B. J. Org. Chem. (1996), 61(17), 5729–5735 and Baker, Raymond; Boyes, Alastair L.; Swain, Christopher J. Synthesis of talaromycins A, B, C, and E. J. Chem. Soc., Perkin Trans. 1 (1990), (5), 1415–21.). A solution of 32.9 g (80 mmol) of trans-[4-(2,2-Dibromo-vinyl)-cyclohexylmethyl]-methyl-carbamic acid tert-butyl ester in 640 ml THF was treated at −78° C. with 105 ml (168 mmol) of BuLi (ca 1.6 M in hexane). After 2 h at this temperature 24 g (800 mmol) of paraformaldehyde were added. The reaction mixture was warmed up to RT for 3 h and after 0.5 h at this temperature extracted with water/$Et_2O$ (3×). The organic phases were washed with aqueous 10% NaCl, dried over $Na_2SO_4$ and evaporated. Purification by flash-chromatography on silica gel (hexane/EtOAc 9:1 to 2:1) yielded 12.1 g (54%) of trans-[4-(3-Hydroxy-prop-1-ynyl)-cyclohexylmethyl]-methyl-carbamic acid tert-butyl ester, MS: 282 ($MH^+$).

15.6

In analogy to example 1.6, trans-[4-(3-Hydroxy-prop-1-ynyl)-cyclohexylmethyl]-methyl-carbamic acid tert-butyl ester was converted to trans-3-(4-Methylaminomethyl-cyclohexyl)-prop-2-yn-1-ol, mp: 97–99° C.; MS: 182 ($MH^+$).

15.7

In analogy to example 1.15, trans-3-(4-Methylaminomethyl-cyclohexyl)-prop-2-yn-1-ol with 5.4 eq N-ethyldiisopropylamine and 1.2 eq 2,5-dibromo-pyrimidine [Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] yielded, with no NaI after 3 h at 120° C. in the microwave oven, trans-3-(4-{[(5-Bromo-pyrimidin-2-yl)-methyl-amino]-methyl}-cyclohexyl)-prop-2-yn-1-ol, mp: 121–122° C.; MS: 338 (MH$^+$, 1Br).

15.8

In analogy to example 1.26, trans-3-(4-{[(5-Bromo-pyrimidin-2-yl)-methyl-amino]-methyl}-cyclohexyl)-prop-2-yn-1-ol gave trans-Methanesulfonic acid 3-(4-{[(5-bromo-pyrimidin-2-yl)-methyl-amino]-methyl}-cyclohexyl)-prop-2-ynyl ester, MS: 416 (MH$^+$, 1Br).

15.9

In analogy to example 1.15, trans-3-(4-Methylaminomethyl-cyclohexyl)-prop-2-yn-1-ol with 5 eq N-ethyldiisopropylamine and 4 eq 2-chloro-5-ethylpyrimidine gave, with no NaI after 3.75 h at 120° C. in the microwave oven, trans-3-(4-{[(5-Ethyl-pyrimidin- 2-yl)-methyl-amino]-methyl}-cyclohexyl)-prop-2-yn-1-ol, mp: 69–71° C.; MS: 228 (MH$^+$).

15.10

In analogy to example 1.26, trans-3-(4-1{[(5-Ethyl-pyrimidin-2-yl)-methyl-amino]-methyl}-cyclohexyl)-prop-2-yn-1-ol gave trans-Methanesulfonic acid 3-(4-{[(5-ethyl-pyrimidin-2-yl)-methyl-amino]-methyl}-cyclohexyl)-prop-2-ynyl ester, MS: 366 (MH$^+$).

15.11

In analogy to example 1.15, trans-3-(4-Methylaminomethyl-cyclohexyl)-prop-2-yn-1-ol with 3.4 eq N-ethyldiisopropylamine and 4 eq 3,6-dichloropyridazine gave, with no NaI after 30 min at 120–140° C. in the microwave oven, trans-3-(4-{[(6-Chloro-pyridazin-3-yl)-methyl-amino]-methyl}-cyclohexyl)-prop-2-yn-1-ol, MS: 294 (MH$^+$, 1Cl).

15.12

In analogy to example 1.26, trans-3-(4-{[(6-Chloro-pyridazin-3-yl)-methyl-amino]-methyl}-cyclohexyl)-prop-2-yn-1-ol gave trans-Methanesulfonic acid 3-(4-{[(6-chloro-pyridazin-3-yl)-methyl-amino]-methyl}-cyclohexyl)-prop-2-ynyl ester, MS: 372 (MH$^+$, 1Cl).

Example 16

A solution of 323 mg (corresponding to 0.49 mmol) of trans-Methanesulfonic acid 3-(4-{[(5-bromo-pyrimidin-2-yl)-methyl-amino]-methyl}-cyclohexyl)-prop-2-ynyl ester in 5 ml of methanol was cooled (0° C.), treated with a catalytic amount of NaI, 0.88 ml (4.94 mmol) of Dimethylamine (33% in EtOH 5.6M) and stirred for 16 h at RT. The solvent was evaporated and the residue extracted with aqueous saturated NaHCO$_3$/Et$_2$O (3×). The organic phase was dried with Na$_2$SO$_4$, filtered and evaporated. Purification by flash column chromatography on silica gel (CH$_2$Cl$_2$/MeOH 40:1) gave 137 mg (76%) of pure trans-(5-Bromo-pyrimidin-2-yl)-[4-(3-dimethylamino-prop-1-ynyl)-cyclohexylmethyl]-methyl-amine, mp: 71–72° C.; MS: 365 (MH$^+$, 1Br).

The following compounds were prepared from the corresponding mesylates and secondary amines:

| Example | Compound | MS MH$^+$ | Mp ° C. | Mesylate | Secondary amine |
|---|---|---|---|---|---|
| 16.1 | trans-2-{[3-(4-{[(5-Bromo-pyrimidin-2-yl)-methyl-amino]-methyl}-cyclohexyl)-prop-2-ynyl]-ethyl-amino}-ethanol | 409, 1Br | | trans-Methanesulfonic acid 3-(4-{[(5-bromo-pyrimidin-2-yl)-methyl-amino]-methyl}-cyclohexyl)-prop-2-ynyl ester | Ethyl-(2-hydroxy-ethyl)-amine |
| 16.2 | trans-(5-Bromo-pyrimidin-2-yl)-methyl-[4-(3-piperidin-1-yl-prop-1-ynyl)-cyclohexylmethyl]-amine | 391, 1Br | | trans-Methanesulfonic acid 3-(4-{[(5-bromo-pyrimidin-2-yl)-methyl-amino]-methyl}-cyclohexyl)-prop-2-ynyl ester | Piperidine |
| 16.3 | trans-[4-(3-Dimethylamino-prop-1-ynyl)-cyclohexylmethyl]-(5-ethyl-pyrimidin-2-yl)-methyl-amine | 315 | 57–59 | trans-Methanesulfonic acid 3-(4-{[(5-ethyl-pyrimidin-2-yl)-methyl-amino]-methyl}-cyclohexyl)-prop-2-ynyl ester | Dimethylamine, 33% in EtOH 5.6 M |
| 16.4 | trans-2-{Ethyl-[3-(4-{[(5-ethyl-pyrimidin-2-yl)-methyl-amino]-methyl}-cyclohexyl)-prop-2-ynyl]-amino}-ethanol | 359 | | trans-Methanesulfonic acid 3-(4-{[(5-ethyl-pyrimidin-2-yl)-methyl-amino]-methyl}-cyclohexyl)-prop-2-ynyl ester | Ethyl-(2-hydroxy-ethyl)-amine |
| 16.5 | trans(5-Ethyl-pyrimidin-2-yl)-methyl-[4-(3-piperidin-1-yl-prop-1-ynyl)-cyclohexylmethyl]-amine | 355 | 59–60 | trans-Methanesulfonic acid 3-(4-{[(5-ethyl-pyrimidin-2-yl)-methyl-amino]-methyl}-cyclohexyl)-prop-2-ynyl ester | Piperidine |

-continued

| Example | Compound | MS MH+ | Mp ° C. | Mesylate | Secondary amine |
|---|---|---|---|---|---|
| 16.6 | trans-(6-Chloro-pyridazin-3-yl)-[4-(3-dimethylamino-prop-1-ynyl)-cyclohexylmethyl]-methyl-amine | 321, 1Cl | 81–82 | trans-Methanesulfonic acid 3-(4-{[(6-chloro-pyridazin-3-yl)-methyl-amino]-methyl}-cyclohexyl)-prop-2-ynyl ester | Dimethylamine, 33% in EtOH 5.6 M |
| 16.7 | trans-2-{[3-(4-{[(6-Chloro-pyridazin-3-yl)-methyl-amino]-methyll-cyclohexyl)-prop-2-ynyl]-ethyl-amino}-ethanol | 365, 1Cl | | trans-Methanesulfonic acid 3-(4-{[(6-chloro-pyridazin-3-yl)-methyl-amino]-methyl}-cyclohexyl)-prop-2-ynyl ester | Ethyl-(2-hydroxy-ethyl)-amine |
| 16.8 | trans-(6-Chloro-pyridazin-3-yl)-methyl-[4-(3-piperidin-1-yl-prop-1-ynyl)-cyclohexylmethyl]-amine | 361, 1Cl | 107–109 | trans-Methanesulfonic acid 3-(4-{[(6-chloro-pyridazin-3-yl)-methyl-amino]-methyl}-cyclohexyl)-prop-2-ynyl ester | Piperidine |

Example 17

17.1

To a suspension of 50 g (0.33 mol) trans-4-aminocyclohexanol.hydrochloride and 77 g (0.726 mol, 2.2 eq) $Na_2CO_3$ in 650 ml THF and 150 ml water, 51.2 ml (0.363 mol, 1.1 eq) benzyl chloroformate were added at 5° C. over a period of 20 min. The reaction mixture was stirred at RT for 2 h, diluted with EtOAc and the phases were separated. The organic layer was washed with brine, dried over $Na_2SO_4$, filtered and evaporated. Trituration from hexane yielded 162.4 g (98%) trans-4-Hydroxy-cyclohexylcarbamic acid benzyl ester as white crystals, MS: 249 (M) (in analogy to: Venuti, Michael C.; Jones, Gordon H.; Alvarez, Robert; Bruno, John J.; J. Med. Chem.; 30; 2; 1987; 303–318).

17.2

To a suspension of 37.9 g (0.94 mol, 2.0 eq) LAH in 1.3 l THF was added a suspension of 117 g (0.47 mol) trans-4-Hydroxy-cyclohexylcarbamic acid benzyl ester in 1 l THF over a period of 6 h via a cannula keeping the temperature between 5–10° C. The reaction was refluxed over night and a mixture of $Na_2SO_4$, silica gel and water (160 g, 50 g, 80 ml) was added, stirred for additional 30 min, filtered and concentrated. The crude material was titurated with hexane to yield 27.9 g (46%) trans-4-Methylamino-cyclohexanol. Column chromatography of the mother liquor on silica gel yielded additional 17.1 g (28%) trans-4-Methylamino-cyclohexanol as white solid, MS: 129 (MH+) (in analogy to Venuti, Michael C.; Jones, Gordon H.; Alvarez, Robert; Bruno, John J.; J. Med. Chem.; 30; 2; 1987; 303–318).

17.3

In analogy to example 5.4, trans-4-Methylamino-cyclohexanol and 2,5-dibromo-pyrimidine was converted to trans-4-[(5-Bromo-pyrimidin-2-yl)-methyl-amino]-cyclohexanol, mp: 140–142° C.; MS: 286 (MH+, 1Br).

17.4

A solution of 2.47 g (8.62 mmol) of trans-4-[(5-Bromo-pyrimidin-2-yl)-methyl-amino]-cyclohexanol, 5.53 g (25.86 mmol) of trans-1,4-dibromo-2-butene and 0.87 g (2.57 mmol, 0.3 eq) tetrabutylammoniumhydrogensulfate in 55 ml $CH_2Cl_2$ were treated with 55 ml of 50% aqueous NaOH. The mixture was stirred at RT for 40 h, 2.76 g (12.93 mmol) of trans-1,4-dibromo-2-butene were added and stirred for further 60 h. Then $CH_2Cl_2$ was added and the layers were separated. The inorganic layer was extracted with $CH_2Cl_2$ (3×), the combined organic layers washed with brine and dried over $Na_2SO_4$. The residue was purified by column chromatography on silica gel with hexane:EtOAc (9:1 to 2:1) as eluent yielding 0.8 g (22%) trans-(2E)-[4-(4-Bromo-but-2-enyloxy)-cyclohexyl]-(5-bromo-pyrimidin-2-yl)-methyl-amine as light yellow solid, MS: 418 (MH+, 2Br).

Example 18

In analogy to example 2, the following compounds were prepared from the corresponding bromide and secondary amines:

| Example | Compound | MS MH+ | Bromide | Secondary amine |
|---|---|---|---|---|
| 18.1 | trans-(2E)-(5-Bromo-pyrimidin-2-yl)-methyl-[4-(4-piperidin-1-yl-but-2-enyloxy)-cyclohexyl]-amine | 423, 1Br | trans-(2E)-[4-(4-Bromo-but-2-enyloxy)-cyclohexyl]-(5-bromo-pyrimidin-2-yl)-methyl-amine | Piperidine |
| 18.2 | trans-(2E)-(5-Bromo-pyrimidin-2-yl)-[4-(4-dimethylamino-but-2-enyloxy)-cyclohexyl]-methyl-amine | 383, 1Br | trans-(2E)-[4-(4-Bromo-but-2-enyloxy)-cyclohexyl]-(5-bromo-pyrimidin-2-yl)-methyl-amine | Dimethylamine, 33% in EtOH 5.6 M |

Example 19

A solution of 0.2 g (0.7 mmol) of trans-4-[(5-Bromo-pyrimidin-2-yl)-methyl-amino]-cyclohexanol and 0.24 g (1.4 mmol) 1-(2-chloroethyl)pyrrolidine hydrochloride in 3.5 ml of DMA was treated at 0° C. with 0.24 g (5.59 mmol) of NaH (55% in oil) in small portions. The reaction was stirred for 30 min at 0° C. After warming up to RT a catalytic amount of NaI was added to the reaction and stirred for 1 h at 80° C. The reaction was cooled and poured into water/$Et_2O$ (3×). The organic phase was dried over $Na_2SO_4$ evaporated and purified by flash silica gel column ($CH_2Cl_2$/MeOH 99:1 to 9:1) to yield 13 g (5%) of trans-(5-Bromo-pyrimidin-2-yl)-methyl-[4-(2-pyrrolidin-1-yl-ethoxy)-cyclohexyl]-amine, MS: 383 ($MH^+$, 1Br).

Example 20

20.1

In analogy to example 12, trans-Methanesulfonic acid 4-{2-[(5-bromo-pyrimidin-2-yl)-methyl-amino]-ethyl}-cyclohexylmethyl ester and ethyl-(2-hydroxyethyl)-amine with 1 eq of NaI in DMA at 60° C. for 22 h gave trans-2-[(4-{2-[(5-Bromo-pyrimidin-2-yl)-methyl-amino]-ethyl}-cyclohexylmethyl)-ethyl-amino]-ethanol, MS: 399 ($MH^+$, 1Br).

20.1

In analogy to example 12, trans-Methanesulfonic acid 4-{2-[(5-bromo-pyrimidin-2-yl)-methyl-amino]-ethyl}-cyclohexylmethyl ester and 3-amino-1-propanol with 1 eq of NaI in DMA at 60° C. for 46 h gave trans-3-[(4-{2-[(5-Bromo-pyrimidin-2-yl)-methyl-amino]-ethyl}-cyclohexylmethyl)-amino]-propan-1-ol, MS: 385 ($MH^+$, 1Br).

Example 21

A solution of 0.21 g (0.6 mmol) trans-3-[(4-{2-[(5-Bromo-pyrimidin-2-yl)-methyl-amino]-ethyl}-cyclohexylmethyl)-amino]-propan-1-ol was taken up in 3 ml of dioxan, treated with 3 ml of a aqueous 1N $NaH_2PO_3$ solution and 3 ml of a 36% aqueous formaldehyde solution (Loibner, H., A. Pruckner, et al. (1984). "Reductive methylation of primary and secondary amines with formaldehyde and phosphorous acid salts." *Tetrahedron Lett.* 25(24): 2535–6). The mixture was heated to 60° C. for 30 min. The mixture was cooled and extracted with 2N NaOH/ether (3×). The organic phase was washed with aqueous 10% NaCl, dried ($NaSO_4$) and evaporated. Purification by flash silica gel column ($CH_2Cl_2$/MeOH 98:2 to 9:1) gave 0.17 g (76%) of trans-3-[(4-{2-[(5-Bromo-pyrimidin-2-yl)-methyl-amino]-ethyl}-cyclohexylmethyl)-methyl-amino]-propan-1-ol, MS: 399 ($MH^+$, 1Br).

Example 20

20.1

In analogy to example 1.15, trans-3-(4-Methylaminomethyl-cyclohexyl)-prop-2-yn-1-ol with 5.4 eq N-ethyldiisopropylamine and 1.2 eq 2-chloro-5-n-propylpyrimidine gave, with no NaI after 4 h at 120° C. in the microwave oven, trans-3-(4-{[Methyl-(5-propyl-pyrimidin-2-yl)-amino]-methyl}-cyclohexyl)-prop-2-yn-1-ol, mp: 78–79° C.; MS: 302 ($MH^+$).

22.2

In analogy to example 1.26, trans-3-(4-{[Methyl-(5-propyl-pyrimidin-2-yl)-amino]-methyl}-cyclohexyl)-prop-2-yn-1-ol gave trans-Methanesulfonic acid 3-(4-{[methyl-(5-propyl-pyrimidin-2-yl)-amino]-methyl}-cyclohexyl)-prop-2-ynyl ester, MS: 380 ($MH^+$).

22.3

In analogy to example 1.15, trans-3-(4-Methylaminomethyl-cyclohexyl)-prop-2-yn-1-ol with 5.4 eq N-ethyldiisopropylamine and 1.2 eq 2-bromo-5-chloro-pyrimidine [synthesized from 5-chloro-2-hydroxy-pyrimidine in analogy to Brown, Desmond J.; Arantz, B. W., Pyrimidine reactions. XXII. Relative reactivities of corresponding chloro-, bromo-, and iodopyrimidines in aminolysis. J. Chem. Soc. C (1971), Issue 10, 1889–91] gave, with no NaI after 2 h at 120° C. in the microwave oven, trans-3-(4-{[(5-Chloro-pyrimidin-2-yl)-methyl-amino]-methyl}-cyclohexyl)-prop-2-yn-1-ol, mp: 108–110° C.; MS: 294 ($MH^+$, 1Cl).

22.4

In analogy to example 1.26, trans-3-(4-{[(5-Chloro-pyrimidin-2-yl)-methyl-amino]-methyl}-cyclohexyl)-prop-2-yn-1-ol gave trans-Methanesulfonic acid 3-(4-{[(5-chloro-pyrimidin-2-yl)-methyl-amino]-methyl}-cyclohexyl)-prop-2-ynyl ester, MS: 372 ($MH^+$, 1Cl).

Example 23

23.1

In analogy to example 16, trans-Methanesulfonic acid 3-(4-{[methyl-(5-propyl-pyrimidin-2-yl)-amino]-methyl}-cyclohexyl)-prop-2-ynyl ester and Dimethylamine (33% in EtOH 5.6M) in DMA gave trans-[4-(3-Dimethylamino-prop-1-ynyl)-cyclohexylmethyl]-methyl-(5-propyl-pyrimidin-2-yl)-amine, mp: 49–50° C.; MS: 329 ($MH^+$).

The following compounds were prepared from the corresponding mesylates and secondary amines:

| Example | Compound | MS $MH^+$ | Mp ° C. | Mesylate | Secondary amine |
| --- | --- | --- | --- | --- | --- |
| 23.2 | trans-2-{Ethyl-[3-(4-{[methyl-(5-propyl-pyrimidin-2-yl)-amino]-methyl}-cyclohexyl)-prop-2-ynyl]-amino}-ethanol | 373 | <30 | trans-Methanesulfonic acid 3-(4-{[methyl-(5-propyl-pyrimidin-2-yl)-amino]-methyl}-cyclohexyl)-prop-2-ynyl ester | Ethyl-(2-hydroxyethyl)-amine |
| 23.3 | trans-(5-Chloro-pyrimidin-2-yl)-[4-(3-dimethylamino-prop-1-ynyl)-cyclohexylmethyl]-methyl-amine | 321, 1Cl | 74–75 | trans-Methanesulfonic acid 3-(4-{[(5-chloro-pyrimidin-2-yl)-methyl-amino]-methyl}-cyclohexyl)-prop-2-ynyl ester | Dimethylamine, 33% in EtOH 5.6 M |

-continued

| Example | Compound | MS MH+ | Mp °C. | Mesylate | Secondary amine |
|---|---|---|---|---|---|
| 23.4 | trans-2-{[3-(4-{[(5-Chloro-pyrimidin-2-yl)-methyl-amino]-methyl}-cyclohexyl)-prop-2-ynyl]-ethyl-amino}-ethanol | 365, 1Cl | | trans-Methanesulfonic acid 3-(4-{[(5-chloro-pyrimidin-2-yl)-methyl-amino]-methyl}-cyclohexyl)-prop-2-ynyl ester | Ethyl-(2-hydroxy-ethyl)-amine |

EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents: | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |

| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of the formula

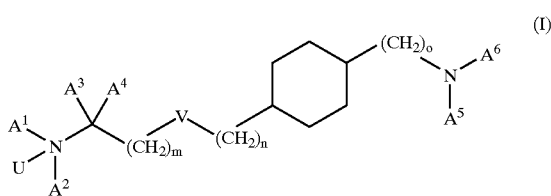

(I)

wherein

U is O or a lone pair,

V is a single bond, O, S, —CH=CH—CH$_2$—O—, —CH=CH—, or —C≡C—, m and n independently from each other are 0 to 7 and m+n is 0 to 7, with the proviso that m is not 0 if V is O or S, o is 0 to 2

$A^1$ is hydrogen, lower-alkyl, hydroxy-lower-alkyl, or lower-alkenyl, $A^2$ is lower-alkyl, cycloalkyl, cycloalkyl-lower-alkyl, or lower-alkenyl, optionally substituted by $R^1$, or $A^1$ and $A^2$ are bonded to each other to form a ring and -$A^1$-$A^2$- is lower-alkylene or lower-alkenylene, optionally substituted by $R^1$, in which one —CH$_2$— group of -$A^1$-$A^2$- can optionally be replaced by NR$^2$, S, or O, $A^3$ and $A^4$ independently from each other are hydrogen or lower-alkyl, or $A^3$ and $A^4$ are bonded to each other to form a ring together with the carbon atom to which they are attached and -$A^3$-$A^4$- is —(CH$_2$)$_{2-5}$—, $A^5$ is hydrogen, lower-alkyl, or lower-alkenyl, $A^6$ is pyrimidinyl, optionally substituted with 1 or 2 substituents independently selected from the group consisting of lower-alkyl, lower-alkyl-cycloalkyl, thio-lower-alkoxy, cycloalkyl, carbamoyl, carboxy, carboxy-lower-alkyl, cyano, amino, mono- and dialkylamino, lower-alkoxy, lower-alkoxy-lower-alkyl, lower-alkoxy-carbonyl, lower-alkoxy-carbonyl-lower-alkyl, lower-alkenyl, lower-alkynyl, aryl, aryl-lower-alkyl, aryloxy, halogen, heteroaryl, heterocyclyl, heterocyclyl-lower-alkyl and trifluoromethyl, $R^1$ is hydroxy, hydroxy-lower-alkyl, lower-alkoxy, lower-alkoxycarbonyl, halogen, CN, N($R^3$,$R^4$), or thio-lower-alkoxy, $R^2$, $R^3$, and $R^4$ independently from each other are hydrogen or lower-alkyl, or a pharmaceutically acceptable salt thereof, with the proviso that the compound of formula (I) is not trans-[4-(2-dipropylamino-ethyl)-cyclohexyl]-pyrimidin-2-yl-amine.

2. The compound according to claim 1, wherein U is a lone pair.

3. The compound according to claim 1, wherein V is a single bond.

4. The compound according to claim 1 wherein V is O.

5. The compound according to claim 1 wherein V is S.

6. The compound according to claim 1 wherein V is —CH=CH—CH$_2$—O—.

7. The compound according to claim 1 wherein V is —CH=CH—.

8. The compound according to claim 1 wherein V is —C≡C—.

9. The compound according to claim 1, wherein $A^6$ is substituted or unsubstituted pyrimidinyl.

10. The compound according to claim 9, wherein $A^6$ is 5-bromo-pyrimidin-2-yl, 5-chloro-pyrimidin-2-yl, 5-pyridin-4-yl-pyrimidin-2-yl, or 5-ethyl-pyrimidin-2-yl.

11. The compound according to claim 1, wherein m is 0 to 3.

12. The compound according to claim 1, wherein m is 0.

13. The compound according to claim 1, wherein n is 0 to 1.

14. The compound according to claim 1, wherein n is 0.

15. The compound according to claim 1, wherein o is 0 or 1.

16. The compound according to claim 1, wherein $A^1$ is lower-alkyl.

17. The compound according to claim 1, wherein $A^1$ is methyl or ethyl.

18. The compound according to claim 1, wherein $A^2$ is lower-alkenyl, or lower-alkyl optionally substituted by $R^2$, wherein $R^2$ is hydroxy or lower-alkoxy.

19. The compound according to claim 1, wherein $A^2$ is methyl, propyl or 2-hydroxy-ethyl.

20. The compound according to claim 1, wherein $A^1$ and $A^2$ are bonded to each other to form a ring and -$A^1$-$A^2$- is lower-alkylene.

21. The compound according to claim 1, wherein -$A^1$-$A^2$- is —(CH$_2$)$_5$—.

22. The compound according to claim 1, wherein $A^3$ and $A^4$ are hydrogen.

23. The compound according to claim 1, wherein $A^5$ is hydrogen or lower-alkyl.

24. The compound according to claim 1, wherein $A^5$ is methyl.

25. The compound according to claim 1, wherein $A^6$ is pyrimidinyl, optionally substituted with 1 or 2 substituents independently selected from the group consisting of lower-alkyl, lower-alkoxy, halogen, pyridyl and thienyl.

26. The compound according to claim 1, wherein $A^6$ is pyrimidinyl, optionally substituted with 1 or 2 substituents independently selected from the group consisting of bromo, chloro, ethyl and pyridyl.

27. The compound according to claim 1, wherein $A^6$ is 5-bromo-pyrimidin-2-yl, 5-chloro-pyrimidin-2-yl, 5-pyridin-4-yl-pyrimidin-2-yl, or 5-ethyl-pyrimidin-2-yl.

28. A pharmaceutical composition for treatment of hypercholesterolemia comprising a pharmacologically effective amount of the compound according to claim 1 and a pharmaceutically acceptable carrier and/or adjuvant.

29. A method for the treatment of hypercholesterolemia comprising administering a composition in accordance with claim 28.

30. A compound selected from the group consisting of
trans-(5-Bromo-pyrimidin-2-yl)-methyl-{4-[3-(methyl-propyl-amino)-prop-1-ynyl]-cyclohexyl}-amine,
  trans-(5-Bromo-pyrimidin-2-yl)-[4-(3-dimethylamino-prop-1-ynyl)-cyclohexyl]-methyl-amine,
  trans-(5-Chloro-pyrimidin-2-yl)-[4-(3-dimethylamino-prop-1-ynyl)-cyclohexyl]-methyl-amine,
  trans-[(5-Bromo-pyrimidin-2-yl)-methyl-[4-(3-piperidin-1-yl-prop-1-ynyl)-cyclohexyl]-amine],
  trans-[4-(3-Dimethylamino-prop-1-ynyl)-cyclohexyl]-methyl-(5-pyridin-4-yl-pyrimidin-2-yl)-amine,
  trans-[4-(3-Dimethylamino-prop-1-ynyl)-cyclohexyl]-(5-ethyl-pyrimidin-2-yl)-methyl-amine,
  trans-(5-Bromo-pyrimidin-2-yl)-[4-(3-dimethylamino-prop-1-ynyl)-cyclohexylmethyl]-methyl-amine,
  trans-2-{[3-(4-{[(5-Bromo-pyrimidin-2-yl)-methyl-amino]-methyl}-cyclohexyl)-prop-2-ynyl]-ethyl-amino}-ethanol,
  trans-2-{Ethyl-[3-(4-{[(5-ethyl-pyrimidin-2-yl)-methyl-amino]-methyl}-cyclohexyl)-prop-2-ynyl]-amino}-ethanol,
  trans(5-Ethyl-pyrimidin-2-yl)-methyl-[4-(3-piperidin-1-yl-prop-1-ynyl)-cyclohexylmethyl]-amine,
or a pharmaceutically acceptable salts thereof.

31. A compound which is trans-2-{Ethyl-[3-(4-{[(5-ethyl-pyrimidin-2-yl)-methyl-amino]-methyl}-cyclohexyl)-prop-2-ynyl]-amino}-ethanol or a pharmaceutically acceptable salts thereof.

32. A pharmaceutical composition for treatment of hypercholesterolemia comprising a pharmacologically effective amount of the compound according to claim 31 and a pharmaceutically acceptable carrier and/or adjuvant.

33. A method for the treatment of hypercholesterolemia comprising administering a composition in accordance with claim 32.

34. A compound which is trans-2-{[3-(4-{[(5-bromo-pyrimidin-2-yl)-methyl-amino]-methyl}-cyclohexyl)-prop-2-ynyl]-ethyl-amino}-ethanol or a pharmaceutically acceptable salt thereof.

35. A pharmaceutical composition for treatment of hypercholesterolemia comprising a pharmacologically effective amount of the compound according to claim 34 and a pharmaceutically acceptable carrier and/or adjuvant.

36. A method for the treatment of hypercholesterolemia comprising administering a composition in accordance with claim 35.

* * * * *